(12) United States Patent
Hayashi et al.

(10) Patent No.: US 7,005,536 B2
(45) Date of Patent: Feb. 28, 2006

(54) METHOD FOR PRODUCING DIOL DERIVATIVES

(75) Inventors: Toshio Hayashi, Kobe (JP); Hideyuki Baba, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 340 days.

(21) Appl. No.: 10/618,491

(22) Filed: Jul. 11, 2003

(65) Prior Publication Data

US 2004/0138409 A1    Jul. 15, 2004

(30) Foreign Application Priority Data

| Jul. 12, 2002 | (JP) | ............................. 2002-204748 |
| Jul. 12, 2002 | (JP) | ............................. 2002-204754 |
| Jul. 12, 2002 | (JP) | ............................. 2002-204784 |

(51) Int. Cl.
   *C07C 69/66*    (2006.01)
(52) U.S. Cl. ........................................ 560/179; 560/185
(58) Field of Classification Search .................... None
   See application file for complete search history.

(56) References Cited

U.S. PATENT DOCUMENTS 3,859,349 A    1/1975    Cody

FOREIGN PATENT DOCUMENTS

| EP | 1 273 579 A1 | 1/2003 |
| WO | WO 99/19378 | 4/1999 |
| WO | WO 01/72736 | 10/2001 |

OTHER PUBLICATIONS

Biella et al, Catalysis Today, Application of Gold Catalysts to Selective Liquid Phase Oxidation, 2002, 72, pp. 43-49.*

* cited by examiner

*Primary Examiner*—Paul A. Zucker
(74) *Attorney, Agent, or Firm*—Knobbe, Martens, Olson & Bear LLP

(57) ABSTRACT

A method of producing a diol derivative efficiently and to high purity is provided. Specifically, the present invention relates to a method of producing a diol derivative having, as a fundamental step, a step of obtaining an α-hydroxycarboxylic acid ester by reacting (i) one or more 1,2-diols or (ii) a 1,2-diol and a primary alcohol as starting material(s) with oxygen in the presence of a catalyst comprising metal loaded on a carrier.

12 Claims, No Drawings

METHOD FOR PRODUCING DIOL DERIVATIVES

TECHNICAL FIELD

The present invention relates to a method of producing diol derivatives such as α-hydroxycarboxylic acid esters, α-hydroxycarboxylic acids, and polyglycolic acid.

BACKGROUND ART

Diol derivatives such as α-hydroxycarboxylic acid esters, α-hydroxycarboxylic acids, and polyglycolic acid are widely used as starting materials for various industrial products and so on.

For example, α-hydroxycarboxylic acids are compounds that are industrially important as, for example, polymerization monomers used as starting materials for various synthetic resins. Conventionally, α-hydroxycarboxylic acid esters are produced through esterification by reacting an α-hydroxycarboxylic acid and an alcohol together.

However, industrial grade α-hydroxycarboxylic acids are aqueous solutions and have low purity, and hence it is difficult to obtain high-purity α-hydroxycarboxylic acid esters using the conventional method. Moreover, in the case of using a high-purity α-hydroxycarboxylic acid, the starting material is expensive, and hence an α-hydroxycarboxylic acid ester cannot be obtained economically.

α-hydroxycarboxylic acids are compounds that are industrially important as, for example, polymerization monomers used as starting materials for various synthetic resins such as polyglycolic acid. In particular, glycolic acid is used, for example, as a metal cleaning agent for cleaning printed circuit boards and the like, and a scale inhibitor for boilers and so on. In addition, in recent years glycolic acid has come to be used as a base cosmetic, a cosmetic liquid or the like having an anti-wrinkle effect.

Conventionally, glycolic acid is predominantly produced using (1) a method in which carbon monoxide, formaldehyde and water are reacted together at high pressure with acid catalysis, or (2) a method in which chloroacetic acid and sodium hydroxide are reacted together. Glycolic acid produced using these methods contains as impurities, for example, formaldehyde, chlorine-containing compounds, organic acids other than glycolic acid such as methoxyacetic acid, and so on.

As glycolic acid for use in cosmetics and so on, there are thus calls for high-purity glycolic acid not containing such impurities.

However, it is difficult to isolate and purify glycolic acid using commonly used purification methods such as distillation, and in particular it is difficult to completely remove impurities such as the above. In actual practice, high-purity glycolic acid obtained by removing the impurities as much as possible from industrial grade glycolic acid containing large amounts of impurities is used.

Industrial grade glycolic acid that is commercially available is predominantly produced using the following two methods. The first method is a carbonylation reaction of folmaldehyde with carbon monoxide high temperature and high pressure in the presence of an acid catalyst. The industrial grade glycolic acid obtained using this production method takes the form of a 70% aqueous solution, and contains a total more than 10 wt % relative to the glycolic acid of glycolic acid dimer, diglycolic acid, methoxyacetic acid, formic acid and so on as organic acids other than glycolic acid. These impurities cannot be separated off using a method such as distillation. A complex purification process must thus be passed through, and moreover there is a problem that the yield is low.

Moreover, although high-purity glycolic acid obtained using this production method is commercially available, the price of such glycolic acid having a purity of 99% or more is high, being more than 10 times that of industrial grade glycolic acid, and hence widespread uses are limited.

The other method of producing glycolic acid is a method in which monochloroacetic acid is hydrolyzed using sodium hydroxide and then neutralization is carried out. With this method, double the stoichiometric amount of sodium hydroxide is consumed as an auxiliary starting material, and hence there is a problem that a large amount of sodium chloride contaminated with organic compound is generated as waste.

There are thus strong calls for the development of a method enabling high-purity glycolic acid not containing impurities such as formaldehyde and chlorine-containing compounds to be produced economically.

Methods of producing polyglycolic acid can be broadly classified into the following two methods. One is a method in which glycolic acid or a glycolic acid ester is subjected to polycondensation directly. The other is a method in which glycolide, which is acyclic dimer of glycolic acid is first produced, and then the glycolide is subjected to ring-opening polymerization.

To produce high-molecular-weight polyglycolic acid using such a method, it is necessary to precisely control the purity of the glycolic acid or glycolic acid ester used as the starting material and the types and amounts of impurities. For example, it is thought that impurities such as methoxyacetic acid esters and diglycolic acid ester inhibit polymerization, and hence it is preferable to remove these impurities as much as possible.

Generally commercially available industrial grade glycolic acid is a 70% aqueous solution. This contains a total of more than 10 wt % relative to the glycolic acid of glycolic acid dimer, diglycolic acid, methoxyacetic acid, formic acid and so on as organic acids other than glycolic acid. To obtain high-quality high-molecular-weight polyglycolic acid, it is essential to use a purified glycolic acid ester as the starting material. Consequently, to produce a high-purity glycolic acid ester from industrial grade glycolic acid, it is necessary to pass through a large number of steps such as recrystallization of the glycolic acid, oligomerization, alcoholysis, and distillation (International Patent Publication No. WO99/19378).

Moreover, high-purity glycolic acid having a purity of 99% or more has also been produced (U.S. Pat. No. 3,859,349). However, the price thereof is high, being more than 10 times that of industrial grade glycolic acid. It is thus not possible to provide polyglycolic acid inexpensively.

In the case of the method of producing polyglycolic acid via glycolide, again complex operations are required for producing and purifying the glycolide. Moreover, regarding the purification of the glycolic acid that is a starting material of the glycolide or the glycolic acid or glycolic acid ester that is a starting material of the polyglycolic acid, as above it is necessary to pass through a large number of steps, and hence the purification is very costly (International Patent Publication No. WO01/72736).

In this way, it is difficult to produce high-molecular-weight high-quality polyglycolic acid economically regardless of which method is used. Moreover, there are also calls for the development of a method of producing high-quality glycolic acid esters inexpensively.

It is thus a principal object of the present invention to produce high-purity diol derivatives at lower cost.

DISCLOSURE OF THE INVENTION

The present inventors discovered that the problems of the prior art could be resolved and the above object could be attained through a production method having a specific step, thus accomplishing the present invention.

Specifically, the present invention relates to the following methods of producing diol derivatives.

1. A method of producing a diol derivative, comprising a step of obtaining an α-hydroxycarboxylic acid ester by reacting (i) one or more types of 1,2-diol or (ii) a 1,2-diol and a primary alcohol as starting material(s) with oxygen in the presence of a catalyst comprising metal supported on a carrier. (Hereinafter this is referred to as the 'first invention'.)

2. The method according to item 1 above, wherein the metal loaded on the carrier is a metal other than gold.

3. The method according to item 1 above, wherein ethylene glycol and a primary alcohol are used as the starting materials.

4. The method of producing a diol derivative according to item 1 above, further comprising a step of hydrolyzing the obtained α-hydroxycarboxylic acid ester to obtain an α-hydroxycarboxylic acid. (Hereinafter this is referred to as the 'second invention'.)

5. The method according to item 4 above, wherein the metal loaded on the carrier comprises gold and at least one metal other than gold.

6. The method of producing a diol derivative according to item 4 above, further comprising a step of subjecting the obtained α-hydroxycarboxylic acid to polycondensation to obtain polyglycolic acid. (Hereinafter this is referred to as the 'third invention'.)

7. The method according to item 6 above, further comprising a step of subjecting the obtained polyglycolic acid to further polycondensation to produce polyglycolic acid having a higher molecular weight.

8. The method according to item 6 above, further comprising a step of subjecting the obtained polyglycolic acid to depolymerization to obtain glycolide.

9. The method of producing a diol derivative according to item 1 above, further comprising a step of subjecting the obtained α-hydroxycarboxylic acid ester to polycondensation to obtain polyglycolic acid. (Hereinafter this is referred to as the 'third invention'.)

10. The method according to item 9 above, further comprising a step of subjecting the obtained polyglycolic acid to further polycondensation to produce polyglycolic acid having a higher molecular weight.

11. The method according to item 9 above, further comprising a step of subjecting the obtained polyglycolic acid to depolymerization to obtain glycolide.

12. The method according to item 9 above, wherein the metal loaded on the carrier comprises gold and at least one metal other than gold.

13. A glycolic acid ester substantially not containing formaldehyde and chlorine as impurities.

14. Glycolic acid substantially not containing formaldehyde and chlorine as impurities.

15. Polyglycolic acid substantially not containing formaldehyde and chlorine as impurities.

16. The method according to item 4 above, wherein the metal loaded on the carrier comprises at least one precious metal.

17. The method according to item 9 above, wherein the metal loaded on the carrier comprises at least one precious metal.

Note that in the present specification, there are places in which explanation is given with glycolic acid taken as a representative example of the α-hydroxycarboxylic acid for convenience; however, the α-hydroxycarboxylic acid ester in the present invention is not limited to being glycolic acid.

<First Invention>

The method of producing a diol derivative of the first invention relates to a method of producing an α-hydroxycarboxylic acid ester. In other words, the first invention is a method of producing an α-hydroxycarboxylic acid ester by oxidation with molecular oxygen using (i) one or more types of 1,2-diol or (ii) a 1,2-diol and a primary alcohol as starting material(s) in the presence of a catalyst comprising metal supported on a carrier (hereinafter sometimes referred to as a 'metal-loaded catalyst').

1. Metal-loaded Catalyst (1) Catalytically Active Component(s)

The catalyst used in the present invention is a catalyst in which metal(s) as active component(s) is/are supported on a carrier, i.e. is a metal-loaded catalyst.

There are no particular limitations on the metal(s) that is/are the active component(s), but precious metals are preferable, with examples being gold, palladium, ruthenium, rhodium, iridium, platinum and so on, and with gold, palladium, ruthenium and so on being particularly preferable. In the first invention, a metal other than gold is particularly preferable. Particularly preferable is at least one of palladium, ruthenium, rhodium, iridium and platinum.

The catalyst used in the present invention contains precious metal(s) as described above as essential component(s), and moreover can also contain as active component(s) at least one element selected from the group consisting of group 2B, group 3B, group 4B, group 5B and group 6B elements from the fourth to sixth periods, and group 8 elements from the fourth period (hereinafter these elements are sometimes referred to as 'secondary elements'). Specific examples of secondary elements are group 2B elements such as Zn, Cd and Hg, group 3B elements such as Ga, In and Tl, group 4B elements such as Ge, Sn and Pb, group 5B elements such as As, Sb and Bi, group 6B elements such as Se, Te and Po, group 8 elements such as Fe, Co and Ni, and the like. As the catalyst used in the present invention, a catalyst containing at least Pb as a secondary element is preferable. For example, a catalyst in which fine metal particles containing Pb and at least one active component selected from the group consisting of Au, Pd and Ru are supported on a carrier can be favorably used.

Regarding the metal(s) that is/are the active component (s), one of the above-mentioned precious metals may be used alone, or two or more may be used. In the case of using two or more precious metals, part or the whole may form an alloy, an intermetallic compound or the like, so long as the effects of the present invention can be obtained.

Moreover, in the case that the metals that are the active components include precious metal(s) and secondary element(s), part or the whole may form an alloy, an intermetallic compound or the like, so long as the effects of the present invention can be obtained. The precious metal(s) and the secondary element(s) are usually supported on the carrier as fine particles. The catalyst used in the present invention may contain impurities or elements other than the precious metal(s) and secondary element(s) so long as this is within a range such that the effects of the present invention are not impaired.

There are no limitations on the particle diameter of the metal particles that constitute the active component(s) so long as the prescribed catalytic activity can be obtained, but the average particle diameter is usually not more than approximately 10 nm, preferably not more than approximately 6 nm, more preferably not more than approximately 5 nm, particularly preferably approximately 1 to 5 nm. If the average particle diameter is set to be within such a range, then an excellent catalytic activity can be obtained more reliably. There are no particular limitations on the lower limit of the average particle diameter, but from the standpoint of physical stability this is preferably made to be approximately 1 nm.

Note that for the average particle diameter of the metal particles in the present invention, 120 arbitrarily selected metal particles are observed on the carrier using a transmission electron microscope (TEM), and out of these 120 particles, (1) the 10 largest particles, and (2) the 10 smallest particles, i.e. a total of 20 particles, are excluded; the average particle diameter then indicates the arithmetic mean of the particle diameter for the remaining 100 particles. Moreover, it is preferable for the maximum in the particle diameter distribution for the metal particles to be in a range of approximately 1 to 6 nm, particularly preferably 1 to 5 nm. It is preferable for the particle diameter distribution to be narrow, with it being preferable for the standard deviation of the particle diameter for the above-mentioned 120 particles to be not more than approximately 2, particularly preferably not more than approximately 1.5.

The amount loaded of the metallic active component(s) in the catalyst may be decided as appropriate in accordance with the usage of the final product, the type of the carrier and so on, but is usually preferably made to be approximately 0.01 to 20 parts by weight, particularly preferably 0.1 to 10 parts by weight, per 100 parts by weight of the carrier.

(2) Carrier

There are no particular limitations on the carrier, with it being possible to use one that is conventionally used as a catalyst carrier. For example, a commercially sold carrier can be used. Moreover, a carrier obtained using a publicly known production method can also be used. Various carriers can be given as examples, for example inorganic oxides such as metal oxides (silica, alumina, titania, zirconia, magnesia etc.), mixed metal oxides (silica/alumina, titania/silica, silica/magnesia etc.), zeolites (ZSM-5 etc.), and mesoporous silicates (MCM-41 etc.); natural minerals (clay, diatomaceous earth, pumice etc.); and carbon materials (activated charcoal, graphite etc.); out of these, inorganic oxides are preferable.

In the present invention, an inorganic oxide carrier comprising an oxide containing at least one element out of Mg, Ca, Sr, Ba, Al, Si, Ti, V, Cr, Mn, Fe, Co, Ni, Cu, Zn, Zr, Nb, Sn, Pb, La and Ce can be preferably used. The above-mentioned oxide may be a mixed oxide in which two or more oxides each of a single element are mixed together, or may be a complex oxide (or composite oxide). An oxide containing at least one element selected from the group consisting of Si, Al, Ti and Zr is preferable as the inorganic oxide carrier.

There are no limitations on the method of producing the carrier, with it being possible to use a publicly known production method. Examples are an impregnation method, a coprecipitation method, an ion exchange method, a vapor phase deposition method, a kneading method, a hydrothermal synthesis method, and so on.

For example, the inorganic oxide carrier can be obtained using a method in which an aqueous solution of water-soluble compound(s) containing at least one of Mg, Ca, Sr, Ba, Al, Ti, V, Cr, Mn, Fe, Co, Ni, Cu, Zn, Zr, Nb, Sn, Pb, La and Ce is impregnated into silica, and then the impregnated body obtained is calcined. With such an inorganic oxide carrier, the fine particles that constitute the catalytically active component(s) can be loaded more reliably, and moreover due to a synergistic effect with the fine particles, a yet higher catalytic activity can be obtained.

There are no limitations on the compound(s) used in the above-mentioned carrier production method. Examples include inorganic compounds such as nitrates, sulfates and hydroxides, and organic compounds such as carboxylates, alkoxides and acetylacetonates.

There are also no limitations on the above-mentioned water-soluble compound(s), so long as the compound(s) is/are water-soluble. Examples are inorganic acid salts such as titanyl sulfate, zirconyl nitrate, zinc nitrate, lanthanum nitrate, iron nitrate, nickel nitrate and aluminum nitrate; and organic acid salts such as titanium n-butoxide, titanium acetylacetonate, zirconium acetylacetonate, lead acetate and magnesium acetate. These salts may be in the form of an anhydride or a hydrate. Moreover, the concentration of the above-mentioned aqueous solution can be set as appropriate in accordance with the type(s) of the water-soluble compound(s) used and so on.

There are no limitations on the amount of the above-mentioned aqueous solution impregnated into the silica, but this amount is usually preferably made to be approximately 1 to 20 parts by weight per 100 parts by weight of the silica.

In the present invention, the inorganic oxide carrier is preferably porous; in particular, the specific surface area thereof (BET method) is preferably at least approximately 50 $m^2/g$, more preferably at least approximately 100 $m^2/g$, most preferably approximately 100 to 800 $m^2/g$. There are no limitations on the shape or size of the carrier, which may be decided as appropriate in accordance with the usage of the final product or the like.

2. Method of Producing Catalyst

There are no limitations on the method of producing the catalyst used in the present invention so long as a loaded carrier as described above can be obtained. For example, the catalyst can be obtained by subjecting a carrier containing at least one desired metal or compound thereof to heat treatment. The metal compound may be any of a hydroxide, a chloride, a carboxylate, a nitrate, an alkoxide, an acetylacetonate, and so on.

Moreover, in the case of loading two or more metals on the carrier, there are no limitations on the order of loading the metals, with it being possible to load either/any first, or both/all simultaneously. For example, in the case of loading a precious metal and a secondary element, any may be used out of (A) a method in which the precious metal is loaded on the carrier, and then the secondary element is loaded, (B) a method in which the secondary element is loaded on the carrier, and then the precious metal is loaded, and (C) a method in which the precious metal and the secondary element are loaded on the carrier simultaneously. Following is a concrete description of each of the methods.

Method (A)

Above-mentioned method (A) is a method in which the precious metal is loaded on the carrier, and then the secondary element is loaded. First, a precious metal-loaded carrier in which the precious metal is loaded is produced. There are no limitations on the method of producing the precious metal-loaded carrier; for example, a conventional method such as a coprecipitation method, an ion exchange method, a deposition-precipitation method, an impregnation method or a vapor phase deposition method can be used, with an ion exchange method, a deposition-precipitation method, an impregnation method or the like being preferable.

In the case of using an ion exchange method, the precious metal-loaded carrier can be obtained, for example, by making the carrier coexist with an aqueous solution containing a cationic complex salt of the precious metal, thus binding, i.e. loading, the cationic complex of the precious metal onto the carrier surface as cations, and then carrying out calcination and/or reduction treatment or the like. When loading the cationic complex of the precious metal onto the carrier surface by ion exchange, the various conditions such as the concentration of the precious metal complex salt in the aqueous solution, the temperature and the pH may be controlled as appropriate. Moreover, before the calcination and/or reduction treatment, the carrier having the cationic complex of the precious metal bound, i.e. loaded, on the surface thereof as cations may be subjected to washing with water, drying and the like.

In the case of using a deposition-precipitation method, the precious metal-loaded carrier can be obtained, for example, by making the carrier coexist with an aqueous solution containing a precious metal compound, thus depositing and precipitating a precious metal-containing precipitate on the carrier surface, and then calcining the carrier on which the precious metal-containing precipitate has been deposited. When depositing and precipitating the precious metal-containing precipitate on the carrier surface, the various conditions such as the concentration of the precious metal in the aqueous solution, the temperature and the pH may be controlled as appropriate. Moreover, the carrier on which the precious metal-containing precipitate has been deposited may be subjected if necessary to washing with water, drying and so on before the calcination.

In the case of using an impregnation method, the precious metal-loaded carrier can be obtained, for example, by making the carrier coexist with a solution containing a precious metal compound, thus adsorbing the precious metal compound onto the carrier surface, and then carrying out calcination and/or reduction treatment or the like. When adsorbing the precious metal compound onto the carrier surface, the various conditions such as the concentration of the precious metal compound in the aqueous solution, the temperature and the pH may be controlled as appropriate. Moreover, the carrier having the precious metal compound adsorbed on the surface thereof may be subjected to washing, drying and so on before the calcination and/or reduction treatment.

There are no particular limitations on the above-mentioned precious metal compound, so long as it is a compound that dissolves in water or an organic solvent. For example, as gold compounds, examples are complexes such as tetrachloroauric (III) acid ($H[AuCl_4]$), sodium tetrachloroaurate (III), ($Na[AuCl_4]$), potassium dicyanoaurate (I) ($K[Au(CN)_2]$) and diethylamine gold (III) trichloride ($(C_2H_5)_2NH[AuCl_3]$), gold (I) cyanide, and so on. One or more of these compounds can be used. As palladium compounds, examples are palladium oxide, palladium chloride, palladium bromide, palladium acetate, palladium nitrate, tetraamminepalladium chloride, tetraamminepalladium nitrate, tetraamminepalladium hydroxide, palladium acetylacetonate, sodium tetrachloropalladate, dichlorobis(triphenylphosphine)palladium, bis(acetonitrile)dichloropalladium, and so on. As ruthenium compounds, examples are ruthenium oxide, ruthenium chloride, ruthenium bromide, ruthenium nitrate, tetraammineruthenium chloride, tetraammineruthenium nitrate, tetraammineruthenium hydroxide, ruthenium acetylacetonate, dichlorotris(triphenylphosphine)ruthenium, and so on.

The precious metal concentration in the above-mentioned aqueous solution will vary according to the type of the compound used and so on, but is usually preferably made to be approximately 0.1 to 100 mmol/L. Moreover, the pH of the aqueous solution is usually set to approximately 5 to 10, preferably approximately 6 to 9. The pH can be adjusted using an alkali such as sodium hydroxide, potassium hydroxide, sodium carbonate, potassium carbonate or ammonia. Moreover, an acid such as hydrochloric acid can be used if necessary. Such alkalis or acids may be used in the form of an aqueous solution if necessary.

The calcination when producing the precious metal-loaded carrier can be carried out, for example, as follows. If necessary, drying may be carried out by heating to a prescribed temperature in advance before the calcination. The drying temperature is usually preferably made to be less than approximately 150° C. The calcination temperature is usually made to be approximately 150 to 800° C., preferably approximately 200 to 700° C., more preferably approximately 250 to 600° C. The calcination may be carried out in air (the atmosphere) or an oxidizing atmosphere, or in an atmosphere of an inert gas such as nitrogen, argon or helium, or in a reducing atmosphere of hydrogen, carbon monoxide or the like. Moreover, the calcination time may be set as appropriate in accordance with the calcination temperature, the size of the solid component and so on. Through the calcination, a prescribed precious metal-loaded carrier in which the precious metal is securely fixed to the carrier surface can be obtained. The precious metal-loaded carrier obtained using one of the methods described above or the like may be used as a catalyst after secondary element(s) has/have been further loaded as described below, or the precious metal-loaded carrier can also be used as a catalyst in the present invention as is.

Next, at least one secondary element or compound thereof is loaded on the precious metal-loaded carrier, and then heat treatment is carried out, thus forming a composite of the precious metal(s) and the secondary element(s).

There is no limitation to the loading method described above, with it being possible to carry out the loading following a conventional method. Examples are an impregnation method, an ion exchange method, a vapor phase deposition method, and so on. Of these, an impregnation method can be favorably used. For example, a mixture of the above-mentioned precious metal-loaded carrier and a solution in which is dissolved compound(s) containing the secondary element(s) is prepared, and then the solid component recovered from the mixture is subjected to heat treatment, whereby the secondary element(s) can be favorably loaded.

There are no particular limitations on the compound(s) containing the secondary element(s), but examples are inorganic compounds such as nitrates, sulfates, hydroxides and chlorides, and organic compounds such as formates, acetates, β-diketone compounds and alkoxides. More specifically, examples are lead acetate, zinc acetate, zinc nitrate, bismuth nitrate, germanium (III) butoxide, nickel bismuth acetylacetonate, iron acetate, and so on.

The solution in which the compound(s) containing the secondary element(s) is/are dissolved can be prepared by using a combination of the compound(s) containing the secondary element(s) and a solvent in which the compound (s) will dissolve. There are no particular limitations on the solvent, with it being possible to use water, an organic solvent or the like. Examples of organic solvents are alcohols, ketones, aromatic hydrocarbons, carboxylic acid esters, nitrites and so on. In particular, it is preferable to use at least one selected from water and alcohols (particularly methanol, ethanol). In the above-mentioned combination, it is thus preferable to use a compound that will dissolve in water or an alcohol. For example, in the case of using Pb as a secondary element, a solution of lead acetate (which may be the hydrate) dissolved in methanol can be favorably used.

The concentration of the secondary element(s) in the solution in which the compound(s) containing the secondary element(s) is/are dissolved can be set as appropriate in accordance with the type of the compound(s), the type of the solvent and soon, but is usually preferably made to be approximately 0.01 to 10 mmol/L.

Moreover, the mixing ratio of the precious metal-loaded carrier and the solution in which the compound(s) containing the secondary element(s) is/are dissolved can be set as appropriate in accordance with the concentration of the solution, the desired amounts loaded of the precious metal(s) and the secondary element(s), and so on.

After preparing the mixture of the precious metal-loaded carrier and the solution in which the compound(s) containing the secondary element(s) is/are dissolved, the solid component is recovered from the mixture. There are no limitations on the method of recovering the solid component, so long as the compound(s) containing the secondary element(s) is/are loaded on the precious metal-loaded carrier. For example, it is preferable to distill off the solvent using an evaporator or the like.

Next, the solid component is subjected to heat treatment. The heat treatment temperature is preferably made to be a temperature such that the metal particles obtained are constituted from the precious metal(s) and the secondary element(s). Specifically, the heat treatment is preferably carried out such that when the precious metal particle-loaded carrier ultimately obtained is used as a catalyst, catalytic activity is exhibited through formation of a composite between the precious metal(s) and the secondary element(s).

The heat treatment temperature will vary according to the type of the secondary element(s) and so on, but is generally set to approximately 50 to 800° C., preferably approximately 100 to 600° C.

There are no particular limitations on the heat treatment atmosphere, which may be any of a reducing atmosphere, an oxidizing atmosphere, an inert atmosphere, and so on. To form a reducing atmosphere, a reducing gas such as hydrogen, carbon monoxide or an alcohol, or else a mixed gas obtained by diluting such a reducing gas with an inert gas such as nitrogen, helium or argon, may be used. Moreover, to form an oxidizing atmosphere, a gas containing oxygen, air or the like may be used. To form an inert atmosphere, an inert gas such as nitrogen, helium or argon may be used. In the present invention, it is particularly preferable to use a reducing atmosphere. Moreover, it is also possible to carry out heat treatment in an oxidizing atmosphere, and then carry out heat treatment in a reducing atmosphere.

Moreover, the heat treatment time can be varied as appropriate in accordance with the heat treatment temperature and so on, but is usually preferably made to be approximately 10 minutes to 24 hours.

Depending on the type of the secondary element (s), to further promote the formation of a composite with the precious metal(s), the solid component may be subjected to reduction treatment using a reducing agent such as formalin, hydrazine, sodium borohydride or formic acid before the heat treatment.

Method (B)

Above-mentioned method (B) is a method in which the secondary element is loaded on the carrier, and then the precious metal is loaded. There are no limitations on the method of loading the secondary element, with it being possible, for example, to use a method as in (A) above. Specifically, the secondary element may first be loaded on the carrier using a method as in (A) above. The starting material for the secondary element, the conditions of the loading and so on may also be made to be as stated in (A) above.

Note, however, that in some cases, as additional treatment that is preferable in terms of the subsequent operation of loading the precious metal, the secondary element can be fixed securely to the carrier by calcining at approximately 300 to 900° C. in an oxidizing atmosphere (i.e. in the presence of a gas containing oxygen or air).

The loading of the precious metal onto the secondary element-loaded carrier thus produced can be carried out using a method as in (A) above. Specifically, the precious metal may be loaded using an ion exchange method, a deposition-precipitation method, an impregnation method or the like, and then drying and calcination may be carried out as in (A) above. Moreover, as in (A) above, to make the formation of a composite between the precious metal and the secondary element more thorough, it is preferable to carry out heat treatment under a reducing atmosphere as in (A) above. Moreover, reduction treatment using a reducing agent can also be included if necessary.

Method (C)

Above-mentioned method (C) is a method in which the precious metal and the secondary element are loaded on the carrier simultaneously. There are no limitations on the method, so long as the two can be loaded simultaneously. For example, a conventional method such as a coprecipitation method, a deposition-precipitation method, an impregnation method or a vapor phase deposition method can be used. In any of these cases, when loading the precious metal on the carrier, a compound containing the secondary element can be made to coexist in the system, whereby the precious metal and the secondary element can be loaded simultaneously. Furthermore, by subjecting the carrier on which the precious metal and the secondary element have been loaded to heat treatment and/or reduction treatment as in method (A) or (B) above, a catalyst can be obtained in which ultrafine precious metal particles containing a precious metal and a secondary element are loaded on a carrier.

In the present invention, an ion exchange method, a deposition-precipitation method, an impregnation method or the like can be favorably used. With the deposition-precipitation method, it is preferable to carry out control such that a compound containing the secondary element is deposited and forms a precipitate under conditions conducive to a compound containing the precious metal (e.g. a hydroxide) depositing and forming a precipitate (for example, in the case that the above-mentioned compound is a hydroxide, a temperature of approximately 30 to 100° C., a pH of approximately 5 to 10, and a precious metal concentration of approximately 0.1 to 100 mmol/L). In this case, it is preferable to use a water-soluble compound containing the secondary element as a starting material, and from an aqueous solution thereof form a precipitate as a hydroxide containing the secondary element. Moreover, when forming the precipitate, it is preferable for the hydroxides of the precious metal and the secondary element to form precipitates simultaneously, whereby a hydroxide containing both the precious metal and the secondary element is produced. The catalyst can be obtained by further subjecting these precipitates to heat treatment and/or reduction treatment.

With the impregnation method, the catalyst can be obtained by adding the carrier to a solution comprising a precious metal compound and a compound containing the secondary element dissolved in an organic solvent, and distilling off the organic solvent or the like if necessary, whereby the precious metal compound and the compound containing the secondary element are simultaneously attached onto the carrier, and then carrying out heat treatment and/or reduction treatment. As a typical example, taking the case of gold as an example, a methanol solution containing an acetylacetonate compound of gold (e.g. dimethylgold acetylacetonate) and an acetylacetonate compound of a secondary element (e.g. nickel acetylacetonate) is impregnated into the carrier, the methanol is distilled off, and then drying and reduction treatment are carried out, whereby a catalyst in which ultrafine gold alloy particles (e.g. ultrafine Au—Ni alloy particles) containing gold and a secondary element are loaded on a carrier can be obtained.

Regarding the starting material compounds, operating conditions and so on used in the deposition-precipitation method or impregnation method described above, ones as indicated in method (A) above can be used.

3. Method of Producing α-hydroxycarboxylic Acid Ester

The method of producing an α-hydroxycarboxylic acid ester of the present invention is characterized in that reaction of (i) one or more types of 1,2-diol or (ii) a 1,2-diol and a primary alcohol is carried out in the presence of a metal-loaded catalyst and oxygen. That is, (i) oxygen and one or more types of 1,2-diol are reacted together, or (ii) oxygen, a 1,2-diol and a primary alcohol are reacted together.

There are no particular limitations on the 1,2-diol, so long as it has hydroxyl groups in the 1-position and the 2-position. For example, the 1,2-diol may be a polyhydric alcohol having three or more hydroxyl groups. Specific examples of the 1,2-diol are aliphatic 1,2-diols having 2 to 10 carbon atoms such as ethylene glycol, 1,2-propylene glycol, 1,2-butanediol and 1,2-hexanediol; aliphatic polyhydric alcohols having 3 to 10 carbon atoms and having hydroxyl groups in the 1-position and the 2-position such as glycerol, erythritol, xylitol and sorbitol; and also derivatives of these 1,2-diols or the like. Examples of derivatives of 1,2-diol include aliphatic 1,2-diols having 2 to 10 carbon atoms and containing a halogen such as 3-chloro-1,2-propanediol; aliphatic 1,2-diols having 2 to 10 carbon atoms and having an aromatic ring such as 2-phenyl-1,2-ethanediol, and the like. One or a plurality of these 1,2-diols can be used. An aliphatic diol having approximately 2 to 6 carbon atoms such as ethylene glycol can be favorably used as a 1,2-diol.

There are no particular limitations on the above-mentioned primary alcohol, provided that it has a primary hydroxyl group. For example, the primary alcohol may be a polyhydric alcohol having two or more hydroxyl groups. Specific examples of the primary alcohol are aliphatic primary alcohols having 1 to 10 carbon atoms such as methanol, ethanol, 1-propanol, 1-butanol, 1-hexanol and 1-octanol; aliphatic polyhydric alcohols having 2 to 10 carbon atoms and having a primary hydroxyl group such as 1,3-butanediol and 1,4-butanediol; aliphatic unsaturated alcohols having 3 to 10 carbon atoms and having a primary hydroxyl group such as allyl alcohol and methallyl alcohol; alcohols having an aromatic ring such as benzyl alcohol, and the like. One or a plurality of these primary alcohols can be used. An aliphatic primary alcohol having 1 to 4 carbon atoms such as methanol, ethanol, 1-propanol or 1-butanol can be favorably used as a primary alcohol, with a primary alcohol such as methanol, ethanol, 1-propanol or 1-butanol being particularly preferable.

In the production method of the present invention, the 1,2-diol and the primary alcohol may be selected as appropriate in accordance with the type of the desired α-hydroxycarboxylic acid ester and so on. For example, in the case of producing a glycolic acid ester, ethylene glycol may be used as the 1,2-diol, and a primary alcohol such as methanol, ethanol, 1-propanol or 1-butanol may be used as the primary alcohol. Alternatively, in the case of using only ethylene glycol as the 1,2-diol, 2-hydroxyethyl glycolate can be produced.

There are no particular limitations on the reaction ratio of the 1,2-diol and the primary alcohol. Usually, the molar ratio of the primary alcohol to the 1,2-diol is approximately 1:2 to 1:50, preferably 1:3 to 1:20. By making this ratio to be in such a range, it becomes possible to synthesize the α-hydroxycarboxylic acid ester more efficiently.

In the present invention, the reaction of (i) one or more types of 1,2-diol or (ii) a 1,2-diol and a primary alcohol is carried out in the presence of a metal-supported catalyst and oxygen (molecular oxygen).

The reaction may be any of a liquid phase reaction, a gas phase reaction, and the like. The oxygen (oxygen gas) may be diluted with an inert gas such as nitrogen gas, argon gas, helium gas or carbon dioxide gas. Moreover, an oxygen-containing gas such as air can be used. There are no particular limitations on the method of supplying the oxygen into the reaction system, with it being possible to use a publicly known method. In particular, bubbling into a liquid or the like can be favorably used.

There are no particular limitations on the form of the reaction, with any of continuous type, batch type, semi-batch type and so on being possible. In the case of using batch type as the reaction form, the catalyst may be put into the reaction apparatus in one go together with the starting material(s). Moreover, in the case of using continuous type as the reaction form, the catalyst may be filled into the reaction apparatus in advance, or the catalyst may be fed into the reaction apparatus continuously together with the starting material(s). The form of the catalyst may be any of a fixed bed, a fluid bed, a suspended bed and so forth.

The amount used of the catalyst may be set as appropriate in accordance with the type of the starting material(s), i.e. the 1,2-diol and/or the primary alcohol, the type of the catalyst, the reaction conditions, and so on. There are no particular limitations on the reaction time, which will vary according to the conditions set, but usually this time is made to be approximately 0.5 to 20 hours, preferably approximately 1 to 10 hours, in terms of the reaction time or the residence time (amount of liquid resident in reactor/liquid feed rate).

Various conditions such as the reaction temperature and the reaction pressure may be set as appropriate in accordance with the type of the starting material(s), i.e. the 1,2-diol and/or the primary alcohol, the type of the catalyst, and so on. The reaction temperature is usually made to be approximately 0 to 180° C., preferably 20 to 150° C., more preferably 50 to 120° C. By setting the temperature to be in such a range, the reaction can be made to proceed more efficiently. The reaction pressure may be any of a reduced pressure, normal pressure, or an applied pressure, but usually a pressure in a range of approximately 0.05 to 5 Mpa (gauge pressure) is preferable, particularly approximately 0.1 to 2 Mpa. The total pressure is preferably set such that the oxygen concentration in the gas flowing out from the reactor does not exceed the range of explosion (8%). Moreover, the pH of the reaction system is preferably made to be approximately pH2 to 9 from the standpoint of suppressing the amount of byproducts and so on. To adjust the pH, for example an alkali metal compound or an alkaline earth metal compound (carboxylate) can be added to the reaction system as an additive.

The reaction can be carried out in the presence of a solvent. There are cases in which, by using a solvent, the desired carboxylic acid ester can be produced more efficiently. Regarding solvents that can be used, there are no limitations so long as the starting material(s), i.e. the 1,2-diol and/or the primary alcohol, will dissolve in the solvent, and the solvent is not prone to reacting itself under the reaction conditions; the solvent may be selected as appropriate in accordance with the type of the starting material alcohol(s), the reaction conditions and so on. In addition to water, examples are ethers such as diethyl ether, diisopropyl ether and dioxane, aromatic hydrocarbons such as toluene, xylene and benzene, halogen-containing compounds such as methylene chloride, chloroform and ethylene dichloride, and so on. The amount used of the solvent may be set as appropriate in accordance with the type of the solvent, the type(s) of the alcohol(s), the type of the catalyst, and the like.

After the above-mentioned reaction, the catalyst is separated away from the reaction system, and then the α-hydroxycarboxylic acid ester produced may be recovered using publicly known separation purification means or the like. The separating away of the catalyst may be carried out following a publicly known method. For example, in the case that the reaction system comprises the catalyst (solid component) and reaction products (liquid component), the catalyst may be separated away from the reaction products using a publicly known solid/liquid separation method such as filtration or centrifugation.

In the production method of the present invention, for example if ethylene glycol is used as the 1,2-diol, and a primary alcohol (preferably a primary alcohol having 1 to 4 carbon atoms) is used as the primary alcohol, then a glycolic acid ester can be produced. The reaction products will contain the glycolic acid ester as a principal product, and in some cases may also contain the primary alcohol and ethylene glycol as unreacted starting materials. Furthermore, as byproducts, the reaction products will contain water, and in some cases may contain carboxylic acid esters derived from the primary alcohol (for example, in the case that methanol is used as the primary alcohol, methyl formate etc.), oxalic acid esters, and glycolic acid, oxalic acid and oxalic acid monoesters, which are hydrolysis products, and so on.

As a method of isolating the desired glycolic acid ester, an example of a method that can easily be implemented is a method in which the primary alcohol and the water are first distilled off, and then the glycolic acid ester is separated off by distillation. When the glycolic acid ester is distilled, the unreacted ethylene glycol ends up in the distillation bottom. The recovered primary alcohol and the distillation bottom containing the glycolic acid ester can be reused as starting materials in the glycolic acid ester produce.

Glycolic acid esters and oxalic acid esters have similar boiling points, and hence separation cannot be carried out easily by distillation. For example, the boiling point of methyl glycolate is 151° C., and the boiling point of dimethyl oxalate is 164° C. The amount of oxalic acid esters produced in the case of reacting ethylene glycol and a primary alcohol together is low at approximately 10 mol % or less relative to the glycolic acid ester, and depending on the usage this may not be a problem. However, in the case, for example, of using the glycolic acid ester as a starting material for polymerization into polyglycolic acid or the like, if a small amount of oxalic acid compounds is contained, then it may not be possible to obtain high-molecular-weight polyglycolic acid. In such a case, the oxalic acid esters may be removed by some kind of method.

The oxalic acid esters may thus be removed if necessary. As methods of purifying a glycolic acid ester (α-hydroxycarboxylic acid ester) containing oxalic acid esters and/or oxalic acid, there are the following examples: (A) a method in which a metal salt and/or an ammonium salt is added, and an oxalic acid metal salt and/or an oxalic acid ammonium salt thus produced is/are separated off, (B) a method in which ammonia is added, and the oxamic acid esters and/or oxamide thus produced is/are separated off, (C) a method in which an anion exchange resin is used and the oxalic acid is adsorbed onto the resin, and so on. The above-mentioned purification methods (A) to (C) may also be used in combination. Following is a description of purification methods (A) and (B).

The removal of the oxalic acid esters can be carried out at any time after the ethylene glycol and the primary alcohol have been reacted together. For example, the removal of the oxalic acid esters may be carried out at any stage such as after the distilling off of the primary alcohol, after the distilling off of the water, or after the removal of the glycolic acid ester by distillation. The removal of the oxalic acid esters is preferably carried out after reacting the ethylene glycol and the primary alcohol together and at a stage before distilling off the primary alcohol and the water or after distilling off the primary alcohol, i.e. in a state in which the reaction mixture contains water, and is more preferably carried out immediately after reacting the ethylene glycol and the primary alcohol together before distilling off the primary alcohol and the water.

Purification Method (A)

Above-mentioned purification method (A) is a method in which a metal salt and/or an ammonium salt is added, and an oxalic acid metal salt and/or an oxalic acid ammonium salt thus produced is/are separated off. In the following, the reaction mixture after the oxidation is sometimes referred to as the 'crude product'.

There are no particular limitations on metal salts and ammonium salts used in purification method (A), so long as these salts are soluble in water, lower alcohols (e.g. methanol, ethanol etc.), and mixed solvents thereof. It is more preferable to use a metal salt than an ammonium salt. The metal salt may be a complex salt.

Examples of metal salts include hydroxides, carboxylates, carbonates, alkoxides, halides, 1,3-diketone salts, and so on. Examples of carboxylates are salts of fatty acids having approximately 1 to 16 carbon atoms such as formic acid, acetic acid, propanoic acid, butanoic acid, pentanoic acid, hexanoic acid, heptanoic acid, octanoic acid, 2-ethylhexanoic acid, lauric acid and 2-hexyldodecanoic acid, salts of hydroxycarboxylic acids such as glycolic acid and lactic acid, and soon. Examples of alkoxides are aliphatic alkoxides having 1 to 4 carbon atoms such as methoxides, ethoxides, isopropoxides and n-butoxides, aromatic alkoxides such as phenoxides, and so on. Examples of halides are fluorides, chlorides, bromides, iodides, and soon. Examples of 1,3-diketone salts are acetylacetonate salts and so on. As metal salts, carboxylates such as glycolates, acetates and 2-ethylhexanoates, hydroxides, acetylacetonate salts, and so on are preferable, with glycolates being particularly preferable.

As the metal ions contained in the metal salt, ions that form a salt with oxalic acid that has low solubility in water, lower alcohols (e.g. methanol, ethanol) and mixed solvents thereof and thus readily precipitates out are preferable. Examples of the metal ions contained in the metal salt are alkali metal ions such as $Li^+$, $Na^+$, $K^+$, $Rb^+$ and $Cs^+$; alkaline earth metal ions such as $Be^{2+}$, $Mg^{2+}$, $Ca^{2+}$, $Sr^{2+}$, $Br^{2+}$ and $Ra^{2+}$; transition metal ions such as $Ti^{4+}$, $V^{5+}$, $Cr^{3+}$, $Mn^{2+}$, $Fe^{2+}$, $Fe^{3+}$, $Co^{2+}$, $Ni^{2+}$, $Cu^+$, $Cu^{2+}$ and $Zn^{2+}$; lanthanide ions such as $La^{3+}$, $Ce^{3+}$, $Ce^{4+}$, $Pr^{3+}$, $Pr^{4+}$, $Nd^{2+}$, $Nd^{3+}$, $Nd^{4+}$, $Pm^{3+}$, $Sm^{2+}$, $Sm^{3+}$, $Eu^{2+}$, $Eu^{3+}$, $Gd^{2+}$, $Gd^{3+}$, $Tb^{3+}$, $Tb^{4+}$, $Dy^{2+}$, $Dy^{3+}$, $Dy^{4+}$, $Ho^{3+}$, $Er^{3+}$, $Tm^{2+}$, $Tm^{3+}$, $Yb^{2+}$, $Yb^{3+}$ and $Lu^{3+}$; or the like. Alkaline earth metal ions and lanthanide ions are preferable as the metal ions.

As the metal salt, magnesium glycolate, zinc acetate, calcium acetate, calcium hydroxide, sodium hydroxide, nickel 2-ethylhexanoate, tris(acetylacetonate)lanthanum, and so on can be favorably used.

Examples of ammonium salts include ammonium acetate, ammonium carbonate, and so forth, with ammonium carbonate or the like being preferable.

There are no particular limitations on the amount added of the metal salt and/or ammonium salt, but the lower limit of the amount added is usually at least approximately 0.1 equivalents, preferably at least approximately 0.5 equivalents, more preferably at least approximately 1 equivalent, relative to the total amount of oxalic acid esters and oxalic acid. The upper limit of the amount added of the metal salt and/or ammonium salt is usually not more than approximately 50 equivalents, preferably not more than approximately 10 equivalents, more preferably not more than approximately 5 equivalents, relative to the total amount of oxalic acid esters and oxalic acid.

The metal salt and/or ammonium salt may be added to the crude product in the form of a solution dissolved in water; a lower alcohol such as methanol or ethanol; a ketone such as acetone; an aromatic organic solvent such as toluene or xylene; a mixed solvent thereof, or the like. In the case that the crude product already contains water, a lower alcohol or the like, the metal salt and/or ammonium salt can be added as is as a solid, but is/are still preferably added in the form of a solution.

Examples of lower alcohols used as a solvent are primary alcohols having approximately 1 to 8 carbon atoms, preferably approximately 1 to 4 carbon atoms. Specific examples are methanol, ethanol, propanol, isopropanol, butanol, and so forth.

When adding the metal salt and/or oxalic acid salt and mixing, heating is usually carried out so that oxalic acid metal/ammonium salts will readily be produced. There are no particular limitations on the mixing temperature so long as oxalic acid salts are produced, but this temperature is usually approximately 20 to 120° C., preferably approximately 40 to 90° C.

There are no particular limitations on the mixing time so long as oxalic acid salts are sufficiently produced and the effects of the present invention are achieved, and this time can be set as appropriate in accordance with the amount of the crude product, the composition of the crude product, and so on. The mixing time is usually approximately 0.1 to 5 hours, preferably approximately 0.5 to 3 hours.

The mixing may be carried out in an oxidizing atmosphere of air or the like, but is preferably carried out in an inert atmosphere of nitrogen, a noble gas (helium, argon etc.) or the like.

When the metal salt or ammonium salt is added to the crude product, because oxalic acid is a stronger acid than glycolic acid, the oxalic acid esters selectively form a metal salt or an ammonium salt via oxalic acid. Moreover, if the amount added of the metal salt and/or ammonium salt is made to be at least approximately 1 equivalent relative to the oxalic acid esters and oxalic acid contained in the crude product, then the oxalic acid esters and oxalic acid can be converted into the metal salt or ammonium salt thereof virtually quantitatively. In particular, in the case of adding a metal salt of an alkaline earth metal or a lanthanide, the oxalic acid salt has a low solubility and thus is deposited as a precipitate, and hence can easily be separated away using a publicly known solid/liquid separation method such as filtration or centrifugation.

Moreover, even if the oxalic acid metal salt and/or oxalic acid ammonium salt produced exhibit some degree of solubility in water, an organic solvent such as an alcohol, or a mixed solvent thereof, the oxalic acid metal salt and/or oxalic acid ammonium salt will be non-volatile, and hence can easily be separated away using distillation.

Purification Method (B)

Above-mentioned purification method (B) is a method in which ammonia is added to the crude product, and the oxamic acid esters and/or oxamide thus produced are separated off. In purification method (B), when ammonia is added to the crude product, the oxalic acid esters undergo ammonolysis, whereby oxamic acid esters and/or oxamide are produced.

There are no particular limitations on the amount added of the ammonia, but the molar ratio relative to the oxalic acid diesters contained in the crude product (ammonia/oxalic acid diesters) is approximately 1 to 10, preferably approximately 1 to 5, more preferably approximately 1.2 to 3. By making this ratio be in such a range, the oxalic acid diesters can be removed more reliably. Moreover, the glycolic acid ester can be purified with a high yield.

There are no particular limitations on the reaction temperature of the ammonolysis so long as oxamic acid esters and/or oxamide are produced, but this temperature is usually approximately 0 to 100° C., preferably approximately 30 to 60° C.

There are no particular limitations on the pressure and addition rate when adding the ammonia to the crude product. The pressure may be either normal pressure or an applied pressure, and the addition rate may be a rate such that the reaction temperature is kept in the above-mentioned range. The addition of the ammonia to the crude product is carried out, for example, in a normal reactor equipped with a stirrer, by instilling liquid ammonia or an ammonia solution (a solution comprising ammonia dissolved in a solvent that is inert in the reaction such as an alcohol) into the mixture, or by directly blowing ammonia gas or diluted ammonia gas (ammonia gas that has been diluted with a gas that is inert in the reaction such as nitrogen gas) into the mixture.

The oxamide produced through the ammonolysis is non-volatile, and moreover has poor solubility. The oxamide can thus be easily separated from the glycolic acid esters using a publicly known solid/liquid separation method such as distillation, filtration or centrifugation. Moreover, the oxamic acid esters can also be easily separated from the glycolic acid esters by distillation.

After removing the oxalic acid esters using one of the methods described above or the like, separation purification to obtain a glycolic acid ester of higher purity with a high yield can be carried out by distilling the glycolic acid ester. As mentioned earlier, before distilling the glycolic acid ester, it is preferable to distill off the primary alcohol and water. A publicly known method can be used in the distillation of the glycolic acid ester. For example, as a batch type distillation apparatus, an ordinary apparatus that is equipped with a feeding still, a rectifying part, a condenser part and so on and enables refluxing to be carried out can be used. The total content of oxalic acid compounds (oxalic acid, oxalic acid esters, oxalic acid metal salts, ammonium oxalate, oxamide etc.) in the glycolic acid ester obtained through the distillation can be reduced down to approximately 10 ppm or less.

Even with the glycolic acid ester obtained by removing the oxalic acid esters and oxalic acid, distilling off water and alcohol, and further carrying out distillation using the methods described above or the like, the glycolic acid ester may still contain unreacted starting materials, i.e. the primary alcohol and ethylene glycol, and also produced water. The amount of the primary alcohol contained in the glycolic acid is usually not more than approximately 1 wt %, and depending on the purification conditions can be made to be not more than approximately 0.2 wt %. Moreover, the content of ethylene glycol is usually not more than approximately 1 wt %, and depending on the purification conditions can be made to be not more than approximately 1000 ppm by weight. The content of water is usually not more than approximately 1 wt %, and depending on the purification conditions can be made to be not more than approximately 0.2 wt %. Note that the content of oxalic acid esters in a glycolic acid ester obtained by distillation purification without carrying out removal of the oxalic acid esters is usually at least 0.1 wt %, more precisely approximately 0.1 to 2 wt %.

Moreover, the glycolic acid ester obtained as described above substantially does not contain either formaldehyde or chlorine. This is because, in the present invention, neither formaldehyde nor chlorine is used as a starting material, and moreover virtually no formaldehyde or chlorine is produced in the reaction. According to the present invention, a glycolic acid ester can be provided in which the content of each of formaldehyde and chlorine is not more than approximately 1 ppm by weight, preferably not more than approximately 100 ppb by weight, more preferably not more than approximately 10 ppb by weight.

An α-hydroxycarboxylic acid ester obtained using the production method of the present invention can be used in the same ways as an α-hydroxycarboxylic acid ester obtained using a conventional method. In particular, the α-hydroxycarboxylic acid ester can be favorably used as a polymerization monomer, i.e. as a starting material for polyglycolic acid.

The production method of the first invention involves a one-step reaction, and hence an α-hydroxycarboxylic acid ester can be obtained easily.

According to the method of the first invention, an α-hydroxycarboxylic acid ester can be obtained with high selectivity.

To purify an α-hydroxycarboxylic acid ester obtained using a conventional method, complex operations such as crystallization have been required. An α-hydroxycarboxylic acid ester obtained using the present invention can be purified using a simple method such as ordinary distillation.

Consequently, according to the method of the first invention, an α-hydroxycarboxylic acid ester can be produced at low cost.

According to the production method of the first invention, a glycolic acid ester substantially not containing formaldehyde and chlorine as impurities can be obtained.

<Second Invention>

The method of producing a diol derivative of the second invention relates to a method of producing an α-hydroxycarboxylic acid. Namely, the second invention is directed to a method of producing an α-hydroxycarboxylic acid by hydrolyzing the α-hydroxycarboxylic acid ester obtained using the first invention.

More specifically, the method of producing a diol derivative of the second invention is a method of producing an α-hydroxycarboxylic acid by hydrolyzing the α-hydroxycarboxylic acid ester that has been obtained by reacting (i) one or more 1,2-diols or (ii) a 1,2-diol and a primary alcohol with oxygen in the presence of a catalyst in which metal is loaded (hereinafter sometimes referred to as a 'metal-loaded catalyst').

1. Metal-Loaded Catalyst (1) Catalytically Active Component(s)

The catalyst used in the present invention is a catalyst in which metal(s) as active component(s) is/are loaded on a carrier, i.e. a metal-loaded catalyst.

There are no particular limitations on the metal(s) that is/are the active component(s), but precious metals are preferable. Examples are precious metals such as gold, palladium, ruthenium, rhodium, iridium, platinum or the like. In the second invention, at least one of gold, palladium and ruthenium is particularly preferable.

The catalyst used in the present invention contains precious metal(s) as described above as essential component(s), and moreover can also contain as active component(s) at least one element selected from the group consisting of group 2B, group 3B, group 4B, group 5B and group 6B elements from the fourth to sixth periods, and group 8 elements from the fourth period (hereinafter these elements are sometimes referred to as 'secondary elements'). Specific examples of secondary elements are group 2B elements such as Zn, Cd and Hg, group 3B elements such as Ga, In and Tl, group 4B elements such as Ge, Sn and Pb, group 5B elements such as As, Sb and Bi, group 6B elements such as Se, Te and Po, group 8 elements such as Fe, Co and Ni, and so on. As the catalyst used in the present invention, a catalyst containing at least Pb as a secondary element is preferable. For example, a catalyst in which fine metal particles containing Pb and at least one active component selected from the group consisting of Au, Pd and Ru are loaded on a carrier can be favorably used.

Regarding the metal(s) that is/are the active component (s), one of the above-mentioned precious metals may be used alone, or two or more may be used. In the case of using two or more precious metals, part or the whole may form an alloy, an intermetallic compound or the like, so long as the effects of the present invention can be obtained.

Moreover, in the case that the metals that are the active components include precious metal(s) and secondary element(s), part or the whole may form an alloy, an intermetallic compound or the like, so long as the effects of the present invention can be obtained. The precious metal(s) and the secondary element(s) are usually loaded on the carrier as fine particles. The catalyst used in the present invention may contain impurities or elements other than the precious metal (s) and secondary element(s) so long as this is within a range such that the effects of the present invention are not impaired.

There are no limitations on the particle diameter of the metal particles that constitute the active component(s) so long as the prescribed catalytic activity can be obtained, but the average particle diameter is usually not more than approximately 10 nm, preferably not more than approximately 6 nm, more preferably not more than approximately 5 nm, particularly preferably approximately 1 to 5 nm. If the average particle diameter is set to be within such a range, then an excellent catalytic activity can be obtained more reliably. There are no particular limitations on the lower limit of the average particle diameter, but from the standpoint of physical stability this is preferably made to be approximately 1 nm.

Note that for the average particle diameter of the metal particles in the present invention, 120 arbitrarily selected metal particles are observed on the carrier using a transmission electron microscope (TEM), and out of these 120 particles, (1) the 10 largest particles, and (2) the 10 smallest particles, i.e. a total of 20 particles, are excluded; the average particle diameter then indicates the arithmetic mean of the particle diameter for the remaining 100 particles. Moreover, in the present invention, it is preferable for the maximum in the particle diameter distribution for the metal particles to be in a range of approximately 1 to 6 nm, particularly preferably 1 to 5 nm. It is preferable for the particle diameter distribution to be narrow, with it being preferable for the standard deviation of the particle diameter for the above-mentioned 120 particles to be not more than approximately 2, particularly preferably not more than approximately 1.5.

The amount loaded of the metallic active component(s) in the catalyst may be decided as appropriate in accordance with the usage of the final product, the type of the carrier and so on, but is usually preferably made to be approximately 0.01 to 20 parts by weight, particularly preferably 0.1 to 10 parts by weight, per 100 parts by weight of the carrier.

(2) Carrier

There are no particular limitations on the carrier, with it being possible to use one that is conventionally used as a catalyst carrier. For example, a commercially sold carrier can be used. Moreover, a carrier obtained using a publicly known production method can also be used. Various carriers can be given as examples, for example inorganic oxides such as metal oxides (silica, alumina, titania, zirconia, magnesia etc.), mixed metal oxides (silica/alumina, titania/silica, silica/magnesia etc.), zeolites (ZSM-5 etc.), and mesoporous silicates (MCM-41 etc.); natural minerals (clay, diatomaceous earth, pumice etc.); and carbon materials (activated charcoal, graphite etc.); out of these, inorganic oxides are preferable.

In the present invention, an inorganic oxide carrier comprising an oxide containing at least one element out of Mg, Ca, Sr, Ba, Al, Si, Ti, V, Cr, Mn, Fe, Co, Ni, Cu, Zn, Zr, Nb, Sn, Pb, La and Ce can be preferably used. The above-mentioned oxide may be a mixed oxide in which two or more oxides each of a single element are mixed together, or may be a complex oxide (or composite oxide). An oxide containing at least one element selected from the group consisting of Si, Al, Ti and Zr is preferable as the inorganic oxide carrier.

There are no limitations on the method of producing the carrier, with it being possible to use a publicly known production method. Examples are an impregnation method, a coprecipitation method, an ion exchange method, a vapor phase deposition method, a kneading method, a hydrothermal synthesis method, and so on.

For example, the inorganic oxide carrier can be obtained using a method in which an aqueous solution of water-soluble compound(s) containing at least one of Mg, Ca, Sr, Ba, Al, Ti, V, Cr, Mn, Fe, Co, Ni, Cu, Zn, Zr, Nb, Sn, Pb, La and Ce is impregnated into silica, and then the impregnated body obtained is calcined. With such an inorganic oxide carrier, the fine particles that constitute the catalytically active component(s) can be loaded more reliably, and moreover due to a synergistic effect with the fine particles, a yet higher catalytic activity can be obtained.

There are no limitations on the compound(s) used in the above-mentioned carrier production method. Examples are inorganic compounds such as nitrates, sulfates and hydroxides, and organic compounds such as carboxylates, alkoxides and acetylacetonates.

There are also no limitations on the above-mentioned water-soluble compound(s), so long as the compound(s) is/are water-soluble. Examples are inorganic acid salts such as titanyl sulfate, zirconyl nitrate, zinc nitrate, lanthanum nitrate, iron nitrate, nickel nitrate and aluminum nitrate; and organic acid salts such as titanium n-butoxide, titanium acetylacetonate, zirconium acetylacetonate, lead acetate and magnesium acetate. These salts may be in the form of an anhydride or a hydrate. Moreover, the concentration of the above-mentioned aqueous solution can be set as appropriate in accordance with the type(s) of the water-soluble compound(s) used and so on.

There are no limitations on the amount of the above-mentioned aqueous solution impregnated into the silica, but this amount is usually preferably made to be approximately 1 to 20 parts by weight per 100 parts by weight of the silica.

In the present invention, the inorganic oxide carrier is preferably porous; in particular, the specific surface area thereof (BET method) is preferably at least approximately 50 $m^2/g$, more preferably at least approximately 100 $m^2/g$, particularly preferably approximately 100 to 800 $m^2/g$. There are no limitations on the shape or size of the carrier, which may be decided as appropriate in accordance with the usage of the final product and so on.

2. Method of Producing Catalyst

There are no limitations on the method of producing the catalyst used in the second invention so long as a loaded carrier as described above can be obtained. For example, the catalyst can be suitably produced using the same catalyst production method as in the first invention.

3. Hydrolysis of α-hydroxycarboxylic Acid Ester

In the second invention, an α-hydroxycarboxylic acid ester obtained using the production method of the first invention is hydrolyzed, thus obtaining an α-hydroxycarboxylic acid.

The hydrolysis step may be carried out after the α-hydroxycarboxylic acid ester has been purified. Through the hydrolysis, dimethyl oxalate and ethylene glycol contained in the α-hydroxycarboxylic acid ester as impurities become oxalic acid, methanol and ethylene glycol. The oxalic acid and the methanol can easily be removed using a publicly known purification method such as distillation.

There are no particular limitations on the hydrolysis of the α-hydroxycarboxylic acid ester so long as an α-hydroxycarboxylic acid ester that has been obtained by reacting (i) one or more 1,2-diols or (ii) a 1,2-diol and a primary alcohol as starting material(s) with oxygen in the presence of a metal-loaded catalyst is used, and it is possible to use publicly known conditions.

In the present invention, hydrolysis means a reaction in which an α-hydroxycarboxylic acid and an alcohol are produced by reacting an α-hydroxycarboxylic acid ester and water together. There are no particular limitations on the method of carrying out the hydrolysis reaction, with it being possible to use a known method.

The reaction temperature is usually approximately 30 to 150° C., preferably approximately 50 to 120° C. The molar ratio of the water and the α-hydroxycarboxylic acid ester (water/α-hydroxycarboxylic acid ester) is usually approximately 1/1 to 1/5, more preferably approximately 3/1 to 20/1. Moreover, a catalyst can be used if necessary, with an acid catalyst being preferably used.

The hydrolysis reaction of the α-hydroxycarboxylic acid ester is an equilibrium reaction. Consequently, by removing the byproduct alcohol from the system, the equilibrium shifts toward the side of the products and hence the hydrolysis proceeds more readily. A reaction method such as reactive distillation is thus suitable, with an example being a method in which reactive distillation is carried out in the presence of water. If a reactive distillation method is used, then the α-hydroxycarboxylic acid can be obtained through hydrolysis of the α-hydroxycarboxylic acid ester by vapor-liquid contact, and moreover the alcohol that is a byproduct (hereinafter sometimes referred to as the 'byproduct alcohol') can be distilled out of the system. The hydrolysis reaction can thus be carried out efficiently.

There are no particular limitations on the molar ratio of the water and the α-hydroxycarboxylic acid ester (water/α-hydroxycarboxylic acid ester) during the reactive distillation, and this molar ratio may be set in accordance with the reaction conditions of the reactive distillation; however, this molar ratio is usually approximately 1/1 to 50/1, more preferably approximately 3/1 to 20/1.

With the hydrolysis described above, to further promote the reaction, the reactive distillation can be carried out in the presence of an acid if necessary. There are no particular limitations on such an acid, with it being possible to use a publicly known homogeneous acid catalyst or heterogeneous acid catalyst. Specifically, examples are inorganic acids such as hydrochloric acid, sulfuric acid and phosphoric acid, organic acids such as acetic acid, solid acids such as activated alumina, silica-alumina and zeolites, and so on. One of these acids may be used alone, or two or more may be used in combination. There are no particular limitations on the method of adding the acid to the α-hydroxycarboxylic acid ester. Moreover, an α-hydroxycarboxylic acid, particularly the α-hydroxycarboxylic acid that is the aimed for substance (e.g. glycolic acid in the case of methyl glycolate) can also be used as the above-mentioned acid. In the case that the α-hydroxycarboxylic acid that is the aimed for substance is used as the acid, it is possible to produce a high-purity α-hydroxycarboxylic acid yet more easily and inexpensively.

After carrying out the reactive distillation described above, to distill off the water, if necessary reactive distillation can be carried out in the presence of an organic solvent (azeotropic agent) that forms an azeotropic composition with water. There are no particular limitations on the organic solvent, with examples being cyclohexane, n-propyl acetate and so on. After carrying out the reactive distillation in the presence of the organic solvent, by forming an azeotropic composition and thus removing the water (i.e. by carrying out an azeotropic dehydration operation), an α-hydroxycarboxylic acid of yet higher purity and higher concentration can be produced.

There are no particular limitations on the reactive distillation apparatus; for example, the apparatus may have a structure in which there is a gas phase part inside the apparatus, and the produced byproduct alcohol (low-boiling-point component) can be continuously separated away and removed to the gas phase part. As the reactive distillation apparatus, for example any of various types of commonly used distillation apparatus is suitable, more specifically a batch type distillation apparatus such as a multistage distillation column or a continuous type distillation apparatus. That is, the reactive distillation of the α-hydroxycarboxylic acid ester can be carried out continuously if necessary.

In the case that the reactive distillation apparatus is a multistage distillation column, there are no particular limitations on the number of stages in the distillation column, and the reaction conditions (operating conditions) such as the reaction temperature and reaction pressure, the residence time of the liquid, the reflux ratio, and the liquid holdup amount; for example, a number of stages and reaction conditions such that the amount of water distilled off with the byproduct alcohol is not excessive (i.e. such that water is not distilled off excessively) may be adopted, with these being determined either experimentally or theoretically. Note, however, that if the number of stages and the reflux ratio are made to be extremely low, then the reaction efficiency will drop, and hence it may become difficult to produce the α-hydroxycarboxylic acid efficiently. Moreover, if the number of stages and the reflux ratio are made to be extremely high, then when implementing the production method of the present invention industrially, the apparatus (equipment) will become excessively large, which will be economically disadvantageous.

As the multistage distillation column, a distillation column having at least 3 stages excluding the column top (uppermost stage) and the column bottom (lowermost stage) is preferable. As such a distillation column, a commonly used distillation column is suitable, for example a packed column packed with a packing material such as Raschig rings, pall rings, interlock saddles, Dixon packing, McMahon packing or Sulzer packing, or a tray column that uses trays such as bubble trays, sieve trays or valve trays. Moreover, a composite distillation column that has both trays and packing material layers may also be used. The above-mentioned number of stages indicates the number of trays in the case of a tray column, and indicates the theoretical number of stages in the case of a packed column.

In the case of carrying out the reactive distillation using a batch type distillation apparatus as the reactive distillation apparatus, the α-hydroxycarboxylic acid ester, water, and if necessary an acid and/or an organic solvent are put into the evaporator of the apparatus, and then the resulting mixed liquid is heated up to the reaction temperature (distillation temperature), and hence hydrolysis is made to proceed while distilling off the byproduct alcohol from the column top of the apparatus. As a result, an aqueous solution containing the α-hydroxycarboxylic acid remains in the evaporator.

In the case of carrying out the reactive distillation using a continuous type distillation apparatus as the reactive distillation apparatus, for example a mixed liquid containing the α-hydroxycarboxylic acid ester, water, and if necessary an acid and/or an organic solvent is continuously fed into a medium stage part of the apparatus (a stage in an intermediate part other than the column bottom and the column top), and while doing this the mixed liquid is subjected to reactive distillation, and the byproduct alcohol is continuously distilled off from the column top of the apparatus, while an aqueous solution containing the α-hydroxycarboxylic acid is continuously drawn off from the column bottom of the apparatus. There are no particular limitations on the method of feeding the α-hydroxycarboxylic acid ester, water, acid and organic solvent into the continuous type distillation apparatus, and these components may be fed into the apparatus separately. The components may thus each be fed into a different stage of the apparatus.

Note that so that the reactive distillation is carried out efficiently, it is preferable to set the stage at which a component having a lower boiling point is fed in to be at a lower stage than the stage at which a component having a higher boiling point is fed in. Moreover, in the case of using an acid, the more regions (stages) in which the acid is present, the greater the frequency of contact between the α-hydroxycarboxylic acid ester and the acid, and hence the higher the reaction efficiency. It is thus preferable to feed the acid in at as high a stage as possible in the continuous type distillation apparatus. Furthermore, the above components may be fed in in a liquid state, or may be fed in in a gaseous state, or may be fed in in a gas-liquid mixed state. Note that in the case that the acid is a solid acid (a heterogeneous acid catalyst), the acid may for example be packed into the continuous type distillation apparatus in advance in place of some or all of the packing material. Moreover, to remove the byproduct alcohol from the system easily, a gas (nitrogen gas etc.) that is inert to the α-hydroxycarboxylic acid ester, the α-hydroxycarboxylic acid and so on may be introduced in from the bottom of the continuous type distillation apparatus.

There are no particular limitations on the reaction conditions during the reactive distillation, which may be set in accordance with the type of the α-hydroxycarboxylic acid ester and so on, but the reaction temperature is preferably at least the boiling point of the byproduct alcohol but not more than the boiling point of water. If the reaction temperature is less than the boiling point of the byproduct alcohol, then it will not be possible to distill the byproduct alcohol off efficiently. On the other hand, if the reaction temperature is greater than the boiling point of water, then water will be distilled off excessively, and hence it will not be possible to carry out the reactive distillation efficiently. Moreover, there will be a risk of bringing about side reactions such as a decomposition reaction of the α-hydroxycarboxylic acid ester or α-hydroxycarboxylic acid. Note that in the case that the acid is an inorganic acid or an organic acid (a homogeneous acid catalyst), the acid may be separated from the α-hydroxycarboxylic acid and thus recovered using a publicly known method such as distillation.

When obtaining an α-hydroxycarboxylic acid by hydrolyzing an α-hydroxycarboxylic acid ester using reactive distillation as described above, the byproduct alcohol is substantially the only byproduct. Because the byproduct alcohol is distilled off, the separation and purification of the α-hydroxycarboxylic acid can be carried out easily. According to the method described above, a high-purity α-hydroxycarboxylic acid is obtained in the form of an aqueous solution.

The α-hydroxycarboxylic acid aqueous solution obtained may be further processed in accordance with the form desired. Examples are (1) a method in which concentration is carried out to obtain a high-concentration aqueous solution (e.g. approximately 70 wt % or more glycolic acid), (2) a method in which an α-hydroxycarboxylic acid crystalline solid is obtained through steps such as crystallization, filtering and drying, and so on.

An example of a method of concentrating the α-hydroxycarboxylic acid aqueous solution is, for example, a method in which the α-hydroxycarboxylic acid aqueous solution is heated as is after the hydrolysis step, thus distilling off water. The concentration may be carried out under reduced pressure if necessary.

An example of a method of crystallizing the α-hydroxycarboxylic acid is a method in which water is distilled off while heating until the α-hydroxycarboxylic acid starts to crystallize as a solid, and then crystallization is carried out by cooling to around room temperature. The crystals obtained can easily be isolated using a publicly known solid-liquid separation method such as filtration.

Moreover, in the case that the water is distilled off by carrying out an azeotropic dehydration operation using an organic solvent, an α-hydroxycarboxylic acid of yet higher purity and higher concentration can be obtained.

An α-hydroxycarboxylic acid obtained as described above substantially does not contain either formaldehyde or chlorine as impurities. This is because, in the present invention, neither formaldehyde nor chlorine is used as a starting material, and moreover virtually no formaldehyde or chlorine is produced in the reaction. According to the present invention, an α-hydroxycarboxylic acid (e.g. glycolic acid) can be provided in which the content of each of formaldehyde and chlorine is not more than approximately 1 ppm by weight, preferably not more than approximately 100 ppb by weight, more preferably not more than approximately 10 ppb by weight.

An α-hydroxycarboxylic acid obtained using the production method of the present invention can be favorably used in a publicly known application, for example as a polymerization monomer, i.e. as a starting material for any of various synthetic resins such as a poly-α-hydroxycarboxylic acid. Of such α-hydroxycarboxylic acids, glycolic acid can be favorably used, for example, as a boiler compound, a tanning agent, a chelating agent, a metal cleaning agent for cleaning printed circuit boards or the like, or a scale inhibitor for boilers or the like, or as an intermediate of any of various products such as drugs, agrochemicals, cosmetics and organic chemicals, or as a starting material in the synthesis of polyesters, polymeric surfactants and so on. Glycolic acid obtained using the production method of the present invention does not contain impurities such as formaldehyde, chlorine-containing compounds and methoxyacetic acid, and hence can be particularly suitably used in an application in which there is direct contact with the human body such as in a cosmetic.

According to the production method of the second invention, glycolic acid substantially not containing formaldehyde and chlorine can be obtained.

Moreover, glycolic acid substantially not containing methoxyacetic acid can be obtained.

Conventional high-purity glycolic acid is expensive, having been purified using a complex method such as crystallization. According to the production method of the second invention, an α-hydroxycarboxylic acid such as glycolic acid of high purity can be obtained inexpensively.

According to the method of the second invention, it is thus possible to obtain glycolic acid oligomer, glycolide, and high-molecular-weight polyglycolic acid at low cost.

In the method of the second invention, if ethylene glycol is used as the 1,2-diol, then glycolic acid containing little ethylene glycol can be obtained.

<Third Invention>

The method of producing a diol derivative of the third invention relates to a method of producing polyglycolic acid or glycolide.

Specifically, the method of producing polyglycolic acid ('II' below) is a method of producing polyglycolic acid by subjecting an α-hydroxycarboxylic acid ester obtained using the first invention to polycondensation. Moreover, a method of producing polyglycolic acid by subjecting an α-hydroxycarboxylic acid obtained using the second invention to polycondensation is also included.

The method of producing glycolide ('III' below) is a method of producing polyglycolic acid by subjecting an α-hydroxycarboxylic acid ester obtained using the first invention to polycondensation, and then producing glycolide by subjecting the polyglycolic acid to depolymerization. Moreover, a method of producing polyglycolic acid by subjecting an α-hydroxycarboxylic acid obtained using the second invention to polycondensation, and then producing glycolide by subjecting the polyglycolic acid to depolymerization is also included.

I. Polyglycolic Acid

In the present invention, polyglycolic acid means a macromolecular compound having a polyester structure in which at least three glycolic acid skeletons are joined together. The molecular weight of the polyglycolic acid in the present invention can be selected as appropriate in accordance with the usage and so on, but is usually approximately 200 to 1,000,000. In the present invention, polyglycolic acid also includes polyglycolic acids of relatively low molecular weight, i.e. so-called glycolic acid oligomers.

In the present invention, polycondensation means a reaction in which an α-hydroxycarboxylic acid ester and/or an α-hydroxycarboxylic acid undergo(es) condensation polymerization through condensation with loss of an alcohol or condensation with loss of water by an intermolecular reaction, thus producing a high-molecular-weight polymer such as polyglycolic acid.

II. The Production of Polyglycolic Acid

Following is a description of the method of producing polyglycolic acid by subjecting an α-hydroxycarboxylic acid or an ester thereof to polycondensation. In the following description, glycolic acid or a glycolic acid ester is taken as an example of the α-hydroxycarboxylic acid or ester thereof.

II-(i) Method of Producing Polyglycolic Acid by Subjecting a Glycolic Acid Ester or Glycolic Acid to Polycondensation The present invention includes a method of producing high-molecular-weight polyglycolic acid by subjecting a glycolic acid ester and/or glycolic acid to polycondensation.

More specifically, the present invention includes a method of producing polyglycolic acid through polycondensation of a glycolic acid ester that has been obtained through oxidation of ethylene glycol and a primary alcohol as starting materials with molecular oxygen in the presence of a metal-loaded catalyst.

Moreover, the present invention includes a method of producing polyglycolic acid having the following steps:

(1) A step of producing a glycolic acid ester through oxidation of ethylene glycol and a primary alcohol as starting materials with molecular oxygen in the presence of a metal-loaded catalyst;

(2) a step of hydrolyzing the glycolic acid ester obtained in step (1) above; and (3) a step of carrying out polycondensation using the products, which contain glycolic acid, obtained in step (2) above.

In addition to glycolic acid, the products obtained in step (2) above may contain compound(s) from which polyglycolic acid can be formed such as glycolic acid ester(s). For example, unreacted glycolic acid ester may be contained in step (2), or separate to the products obtained in step (2), compound(s) from which polyglycolic acid can be formed such as glycolic acid ester(s) maybe added. Moreover, it is also possibly to partially hydrolyze a glycolic acid ester into glycolic acid, and then carry out polycondensation using the mixture containing the glycolic acid ester and the glycolic acid to obtain polyglycolic acid.

In the case that glycolic acid and a glycolic acid ester are both present, there are no particular limitations on the ratio of the two, but the weight ratio of the glycolic acid ester to the glycolic acid is usually approximately 1:0.1 to 1:10, preferably approximately 1:0.2 to 1:8.

There are no particular limitations on the conditions under which the polyglycolic acid is produced, so long as a glycolic acid ester and/or glycolic acid obtained using the method of the first invention or the second invention is/are used as starting material(s); regarding the reaction conditions and so on during the polycondensation, publicly known conditions can be used in accordance with the desired molecular weight and so on.

There are no particular limitations on the weight average molecular weight of the polyglycolic acid obtained using the method of producing polyglycolic acid of II-(i) above; various weight average molecular weights can be obtained by changing whether or not a solvent is used, the type of the solvent, the type and amount of a catalyst, the reaction temperature, the reaction time, the method of processing the distilled off solvent, and so on. The weight average molecular weight of the polyglycolic acid can be selected as appropriate in accordance with the usage and so on. For example, the weight average molecular weight of the polyglycolic acid in the case of using the polyglycolic acid as a material such as a film, a sheet or a molding material that must have a gas barrier ability, mechanical strength and soon is usually approximately 5,000 to 1,000,000, preferably approximately 10,000 to 700,000. In the case of using the polyglycolic acid as the starting material in a 'method of producing polyglycolic acid having a higher molecular weight through polycondensation of the polyglycolic acid' as described later, the weight average molecular weight is usually preferably 200 to 150,000, more preferably 1,000 to 100,000.

The content of impurities (e.g. methoxyacetic acid, diglycolic acid, oxalic acid compounds, etc.) that will cause the polymerization to come to an end is low in glycolic acid or a glycolic acid ester obtained using the method of the first invention or the second invention, and hence it is easy to obtain high-molecular-weight polyglycolic acid.

As a glycolic acid alkyl ester used, one in which the alkyl group has 1 to 4 carbon atoms is preferable. Specific examples of suitable glycolic acid alkyl esters are methyl glycolate, ethyl glycolate, n-propyl glycolate, isopropyl glycolate, n-butyl glycolate, isobutyl glycolate, t-butyl glycolate, and so on. Methyl glycolate and ethyl glycolate are particularly preferable, since removal of the alcohol is easy. One glycolic acid alkyl ester can be used alone, or two or more can be used in combination.

The starting material for the polyglycolic acid may contain a comonomer in addition to the glycolic acid alkyl ester(s). Examples of comonomers are cyclic monomers such as ethylene oxalate, lactides, lactones (e.g. β-propiolactone, β-butyrolactone, pivalolactone, γ-butyrolactone, δ-valerolactone, β-methyl-δ-valerolactone, ε-caprolactone), trimethylene carbonate and 1,3-dioxane; hydroxycarboxylic acids such as lactic acid, glycolic acid, 3-hydroxypropanoic acid, 3-hydroxybutanoic acid, 4-hydroxybutanoic acid and 6-hydroxycaproic acid, and alkyl esters thereof; and substantially equimolar mixtures of an aliphatic diol such as ethylene glycol, propylene glycol or 1,4-butanediol and an aliphatic dicarboxylic acid such as succinic acid or adipic acid or an alkyl ester thereof; two or more of these can be added. There are no particular limitations on the amount added of the comonomer(s), so long as this amount is within a range such that polyglycolic acid having desired properties can be obtained.

A catalyst may be used if necessary in the polycondensation reaction of the glycolic acid ester and/or glycolic acid. In the case of using a catalyst, the reaction rate can be increased. There are no particular limitations on the catalyst used, with it being possible to use a publicly known catalyst. Examples are group II, III, IV and V metals of the periodic table, and oxides and salts thereof. Specific examples are metals such as tin dust, titanium, zinc dust, aluminum, magnesium and germanium, metal alkoxides of the above-mentioned metals such as titanium isopropoxide and titanium tetrabutoxide, metal oxides such as tin oxides (stannous oxide, stannic oxide), antimony oxide, zinc oxide, aluminum oxide, magnesium oxide, titanium oxide, germanium oxide and lead oxide, metal halides such as stannous chloride, stannic chloride, stannous bromide, stannic bromide, antimony fluoride, zinc chloride, magnesium chloride, aluminum chloride, titanium chloride and germanium chloride, sulfates such as tin sulfate, zinc sulfate and aluminum sulfate, carbonates such as magnesium carbonate and zinc carbonate, organic carboxylates such as tin acetates (stannous acetate, stannic acetate), tin octanoate, tin lactate, zinc acetate and aluminum acetate, organic sulfonates such as tin trifluoromethanesulfonate, zinc trifluoromethanesulfonate, magnesium trifluoromethanesulfonate, tin methanesulfonate and tin p-toluenesulfontate, and so on. Other examples are organometallic oxides of the above-mentioned metals such as dibutyltin oxide and tetraphenyltin, alkylmetals of the above-mentioned metals such as diethylzinc, ion exchange resins such as Dowex and amberlite, and so on. A single catalyst may be used alone, or two or more may be used together. Tin compounds and titanium compounds are preferable as catalysts. There are no particular limitations on the amount used of the catalyst(s), but this amount is usually approximately 0.0001 to 10 wt % relative to the glycolic acid ester used, with 0.001 to 2 wt % being preferable from an economic standpoint. By making the amount of the catalyst(s) be in such a range, the polymerization time can be shortened more reliably. Moreover, the polymer can be produced without being colored.

In the case of using such catalyst(s), a publicly known coloration preventing agent may be added. Examples of coloration preventing agents are phosphorus compounds and so on. Examples of phosphorus compounds are phosphoric acid, trimethyl phosphate, triethyl phosphate, triphenyl phosphate, polyphosphoric acid monoethyl ester, polyphosphoric acid diethyl ester, pyrophosphoric acid, triethyl pyrophosphate, pyrophosphoric acid hexamethylamide, phosphorous acid, triethyl phosphite, triphenyl phosphate, and so on. These phosphorus compounds can each be used alone, or two or more can be used in combination. There are no particular limitations on the amount added of the phosphorus compound(s), but this amount is usually 0.1 to 10 equivalents, preferably approximately 0.3 to 3 equivalents, in terms of phosphorus atoms per 1 equivalent of metal atoms in the catalyst(s). By making the amount added of the phosphorus compound(s) be in such a range, coloration can be prevented more reliably. Alternatively, coloration can be prevented without inhibiting the polycondensation reaction more reliably. The phosphorus compound(s) can be added to the reaction system as is, or after having been dissolved or dispersed in a suitable liquid. The phosphorus compound(s) may be added all at once or in divided portions. The phosphorus compound(s) may be added to the reaction system at any time until the polycondensation reaction is substantially completed.

The reaction of producing polyglycolic acid from a glycolic acid ester is a condensation reaction with loss of an alcohol, and hence it is preferable to carry out the reaction while removing the produced alcohol. Moreover, the reaction of producing polyglycolic acid from the glycolic acid is a dehydration reaction, and hence it is preferable to carry out the reaction while removing the produced water. There are no particular limitations on the method of removing the produced water or alcohol, with it being possible to use a publicly known method. Examples are a method in which the water or alcohol is removed by passing an inert gas such as nitrogen, argon or helium through the reaction system, a method in which the water or alcohol is removed by carrying out the reaction under a reduced pressure, a method in which the reaction is carried out in the presence of an organic solvent, and the organic solvent and the produced water or alcohol are distilled off together using azeotropy, and so on. Moreover, the water or alcohol may be removed under reduced pressure under a stream of an inert gas.

The polycondensation reaction of the glycolic acid ester or glycolic acid is preferably carried out in the presence of a solvent, although it is not necessary to use a solvent. In the case of carrying out the reaction in an organic solvent, the condensation reaction with loss of an alcohol of the glycolic acid ester or the condensation reaction with loss of water of the glycolic acid is carried out in the organic solvent, and the produced water or alcohol may be distilled out of the reaction system together with the organic solvent. Furthermore, as the water or alcohol and the organic solvent are distilled out of the reaction system as described above, the reaction may be carried out while introducing organic solvent containing a lower amount of water or alcohol than the amount of water or alcohol present in the distilled off organic solvent into the reaction system as additional solvent.

As the organic solvent used in the polycondensation reaction, a solvent that undergoes azeotropy with the produced water or alcohol is preferable, although a solvent that does not undergo such azeotropy may be used. Moreover, the organic solvent may be a solvent that separates out from the produced water or alcohol, or may be a solvent that does not separate out from the produced water or alcohol. Specific examples of the organic solvent are hydrocarbon solvents such as toluene, xylene and mesitylene, halogenated solvents such as chlorobenzene, bromobenzene, iodobenzene, dichlorobenzene, 1,1,2,2-tetrachloroethane and p-chlorotoluene, ketone solvents such as 3-hexanone, acetophenone and benzophenone, ether solvents such as dibutyl ether, anisole, phenetole, o-dimethoxybenzene, p-dimethoxybenzene, 3-methoxytoluene, dibenzyl ether, benzyl phenyl ether and methoxynaphthalene, thioether solvents such as phenyl sulfide and thioanisole, ester solvents such as methyl benzoate, methyl phthalate and ethyl phthalate, diphenyl ether type solvents such as unsubstituted diphenyl ether, alkylsubstituted diphenyl ethers (e.g. 4-methylphenyl ether, 3-methylphenyl ether, 3-phenoxytoluene, etc.), halogen-substituted diphenyl ethers (4-bromophenyl ether, 4-chlorophenyl ether, 4-bromodiphenyl ether, 4-methyl-4'-bromodiphenyl ether, etc.), alkoxy-substituted diphenyl ethers (4-methoxydiphenyl ether, 4-methoxyphenyl ether, 3-methoxyphenyl ether, 4-methyl-4'-methoxydiphenyl ether, etc.) and cyclic diphenyl ethers (dibenzofuran, xanthene, etc.), and polyalkylene glycols such as polyethylene glycol, polypropylene glycol and polybutylene glycol. One of these solvents may be used alone, or two or more may used as a mixed solvent. Alkyl-aryl ether type solvents and diphenyl ether type solvents are particularly preferable. Specific examples of polyalkylene glycol monoethers are, for example, polyalkylene glycol monoalkyl ethers including polyethylene glycol monoalkyl ethers such as polyethylene glycol monopropyl ether, polyethylene glycol monobutyl ether, polyethylene glycol monohexyl ether, polyethylene glycol monooctyl ether, polyethylene glycol monodecyl ether and polyethylene glycol monolauryl ether, and polypropylene glycol monoalkyl ethers and polybutylene glycol monoalkyl ethers in which the ethyleneoxy group in the above compounds is replaced with a propyleneoxy group or a butyleneoxy group. There is no particular limitation on the amount used of the solvent(s), but this amount is usually such that the concentration of the polymer obtained is approximately 10 to 80 wt %.

An example of preferable means for distilling the water or alcohol produced in the polycondensation reaction of the glycolic acid or the glycolic acid ester out of the reaction system using an organic solvent is a method in which the organic solvent and the water or alcohol are distilled off together using azeotropy. The distilled off organic solvent may also be returned into the reaction system after removing at least some of the dissolved water or alcohol using an adsorbent or the like or reducing the amount of water or alcohol by distillation or the like. Moreover, instead of the organic solvent that has been distilled off using azeotropy, new organic solvent containing little water or alcohol may be introduced. Moreover, it is also possible to remove the water or alcohol using reduced pressure during the initial part of the reaction, and then subsequently remove some of the organic solvent from the reaction mixture containing the organic solvent, thus making the amount of water or alcohol in the reaction mixture be a prescribed value.

As other embodiments, a method in which excess solvent is introduced in advance, and the water or alcohol is removed merely by drawing off the solvent, a method in which the reaction solvent is dried using another solvent, and so on are also included. Furthermore, as a variation, the water or alcohol may be removed with the reaction solvent itself still in the form of a liquid. Moreover, regarding the reaction temperature in the present invention, so that the solvent will undergo azeotropy with the water or alcohol, the reaction is preferably carried out at a prescribed temperature even if the boiling point has dropped.

In the polycondensation reaction of the glycolic acid or the glycolic acid ester, by removing the produced water or alcohol from the organic solvent using an adsorbent or the like, it becomes easier to obtain a polyhydroxycarboxylic acid having a high average molecular weight. Examples of such an adsorbent are molecular sieves such as molecular sieve 3A, molecular sieve 4A, molecular sieve 5A and molecular sieve 13X.

The temperature of the polycondensation reaction of the glycolic acid or the glycolic acid ester can be set as appropriate considering the rate of production of the polymer and the rate of thermal decomposition of the produced polymer; this temperature is usually approximately 80 to 220° C., preferably approximately 110 to 200° C. The condensation reaction is usually carried out at the distillation temperature of the organic solvent used under normal pressure. To make the reaction temperature be in a preferable range, in the case of using a high-boiling-point organic solvent, the reaction may be carried out under reduced pressure. On the other hand, in the case of using a low-boiling-point organic solvent, the reaction may be carried out under pressurization.

There are no particular limitations on the reaction time so long as polyglycolic acid of the desired molecular weight can be obtained, with it being possible to set the reaction time as appropriate in accordance with the monomer, catalyst and solvent used and so on. The reaction time is usually approximately 1 to 60 hours, preferably approximately 2 to 48 hours.

By making the temperature be in the above-mentioned range, the polycondensation reaction can be made to proceed at a suitable rate more reliably. Moreover, colorless polyglycolic acid can be obtained more reliably. The polycondensation temperature need not be constant throughout the reaction, but rather variable temperature conditions in which the temperature is progressively raised as the glycolic acid alkyl ester or glycolic acid is converted into a high-molecular-weight compound may be used.

The polycondensation reaction of the glycolic acid or the glycolic acid ester is preferably carried out under an inert gas atmosphere so that moisture will not get in from outside the system, and may be carried out while carrying out replacement with an inert gas or while bubbling with an inert gas. The condensation reaction can be carried out through continuous operation or through batch operation. Moreover, the dehydration or dealcoholization of the solvent and the introduction of the solvent can also be carried out through continuous operation or through batch operation.

After the polycondensation reaction has been completed, a publicly known method can be used as a processing method to obtain the desired polyglycolic acid. An example is a method in which the reaction liquid is gradually cooled while adding solvent and stirring, thus crystallizing out the polyglycolic acid, the crystals are washed with acid or the like to make the amount of solvent less than 10 ppm, and then neutralization, filtration and drying are carried out.

In the case that an alcohol is produced as a byproduct, the alcohol can be recovered, and reused as a starting material in the step of producing the glycolic acid ester. In the case that the alcohol is reused, purification such as removal of water may be carried out if necessary.

II-(ii) Method of Producing Polyglycolic Acid Having Higher Molecular Weight by Subjecting Polyglycolic Acid to Polycondensation The method of producing polyglycolic acid of the present invention includes a method of producing polyglycolic acid having a higher molecular weight by subjecting to further polycondensation polyglycolic acid that has been obtained by subjecting to polycondensation a glycolic acid ester that has been obtained through oxidation of ethylene glycol and a primary alcohol as starting materials with molecular oxygen in the presence of a metal-loaded catalyst.

With the method of producing polyglycolic acid of II-(ii), so long as the polyglycolic acid used as the starting material is polyglycolic acid obtained using the method described in II-(i) above, there are no particular limitations on the conditions under which the polyglycolic acid is subjected to polycondensation, with it being possible to use publicly known conditions. The form of the polyglycolic acid can be made to be any chosen form, for example lumps, pellets, granules or a powder, but it is preferable to make the polyglycolic acid into fine granules by pulverization or the like, since then the surface area is increased and hence the reaction can be promoted.

The weight-average molecular weight of the polyglycolic acid obtained using the method of producing polyglycolic acid of II-(ii) can be set as appropriate by changing whether or not a solvent is used, the type of the solvent, the type and amount of a catalyst, the reaction temperature, the reaction time, the method of processing the distilled off solvent, and so on. The weight average molecular weight of the polyglycolic acid can be selected as appropriate in accordance with the usage and so on, but is usually approximately 50,000 to 1,000,000, preferably approximately 100,000 to 700,000.

Examples of the polycondensation reaction of the polyglycolic acid include solid phase polymerization, melt polymerization, or the like.

An example of a method of subjecting the polyglycolic acid to solid phase polymerization is a method in which heating is carried out to a temperature that is higher than the glass transition temperature of the polyglycolic acid but lower than the melting point, thus carrying out solid phase polymerization to produce polyglycolic acid. The solid phase polymerization is usually carried out in an inert gas atmosphere, or under reduced pressure, or in an inert solvent.

In the solid phase polymerization, as the term suggests, a polymerization reaction is carried out with the polyglycolic acid kept in a solid state. The upper limit of the reaction temperature in the solid phase polymerization is thus determined by the melting point of the polyglycolic acid. The reaction temperature of the solid phase polymerization is usually not more than approximately $(M-5)°$ C., preferably not more than approximately $(M-10)°$ C. (M: the melting point of the polyglycolic acid). By carrying out the reaction within such a temperature range, side reactions can be suppressed more reliably, and hence a high-molecular-weight polyglycolic acid ester can be produced. Moreover, colorless polyglycolic acid can be produced more reliably. The reaction temperature of the solid phase polymerization is preferably approximately 100 to 230° C., more preferably approximately 150 to 220° C.

In the case that the melting point increases during the solid phase polymerization reaction due to the increase in the molecular weight and an annealing effect, the solid phase polymerization reaction temperature can be increased in stages. However, even in this case, the reaction temperature is controlled to be a temperature less than the melting point of the polyglycolic acid at that time, preferably not more than $(M-5)°$ C., more preferably not more than $(M-10)°$ C. (M: the melting point of the polyglycolic acid). The solid phase polymerization is usually carried out by heating the polyglycolic acid to a prescribed temperature in an atmosphere of an inert gas such as nitrogen or argon, under reduced pressure, or in an inert solvent such as liquid paraffin. As a result, undesirable side reactions can be avoided, and hence it becomes easier to make the molecular weight high.

The polymerization reaction can be carried out without a catalyst, but a catalyst can be added if necessary. Examples of catalysts are tin-based catalysts such as stannous chloride, stannic chloride, stannous sulfate, stannous oxide, stannic oxide, tetraphenyltin, stannous octanoate, stannous acetate and stannic acetate, titanium-based catalysts such as titanium tetrachloride, isopropyl titanate and butyl titanate, germanium-based catalysts such as metallic germanium, germanium tetrachloride and germanium oxide, metal oxide type catalysts such as zinc oxide, antimony trioxide, lead oxide, aluminum oxide and iron oxide, and so on. These polymerization catalysts can each be used alone, or two or more can be used in combination.

In the case of using a polymerization catalyst, the catalyst is preferably added in a proportion of approximately 0.001 to 2 parts by weight, more preferably approximately 0.005 to 0.5 parts by weight, per 100 parts by weight of the polyglycolic acid. By making the proportion of the catalyst be in such a range, the polymerization time can be made sufficiently short more reliably. Moreover, a colorless polymer can be obtained more reliably. The catalyst is added to the reaction system as is, or dissolved in or mixed with a suitable liquid. The catalyst may be added all at once or in divided portions. The catalyst may be added to the reaction system at any time until the polymerization reaction is substantially completed.

In the case of using a polymerization catalyst, a phosphorus compound can be used as a coloration preventing agent. Examples of such phosphorus compounds include phosphoric acid, trimethyl phosphate, triethyl phosphate, triphenyl phosphate, polyphosphoric acid monoethyl ester, polyphosphoric acid diethyl ester, pyrophosphoric acid, triethyl pyrophosphate, pyrophosphoric acid hexamethylamide, phosphorous acid, triethyl phosphate, triphenyl phosphate, or the like. These phosphorus compounds can each be used alone, or two or more can be used in combination. The phosphorus compound(s) is/are preferably added in a proportion of 0.1 to 10 equivalents, more preferably 0.3 to 3 equivalents, in terms of phosphorus atoms per 1 equivalent of metal atoms in the catalyst. If the amount added is too low, then there will be little effect of preventing coloration, whereas if the amount added is too high, then the reaction will become slow. The phosphorus compound(s) can be added to the reaction system as is, or after having been dissolved or dispersed in a suitable liquid. The phosphorus compound(s) may be added all at once or in divided portions. The phosphorus compound(s) may be added to the reaction system at any time until the solid phase polymerization reaction is substantially completed.

High-molecular-weight polyglycolic acid having a weight average molecular weight of at least 150,000 can be obtained through the solid phase polymerization. To be stable and exhibit sufficient mechanical properties for use in a film or use in any of various molded articles, the polyglycolic acid is required to have a sufficiently high molecular weight. The polyglycolic acid obtained through the solid phase polymerization preferably has a weight average molecular weight of at least 200,000.

III. Method of Producing Glycolide

The present invention includes a method of producing glycolide using polyglycolic acid obtained in item II above.

The present invention includes a method of producing glycolide through the depolymerization of the polyglycolic acid. There are no particular limitations on the method of producing glycolide of the present invention, so long as the polyglycolic acid used as the starting material is polyglycolic acid obtained using the method described in item II above; regarding the reaction conditions and so on when depolymerizing the polyglycolic acid, publicly known conditions can be used. Examples are a method in which the polyglycolic acid in a solid state is melted by heating to produce a molten liquid, and the depolymerization product, i.e. glycolide, is made to evaporate from the surface of the molten liquid phase under reduced pressure and is collected, a method in which some or all of the polyglycolic acid is dissolved in an organic solvent, depolymerization is carried out under reduced pressure or a stream of an inert gas, and the glycolide produced is distilled off with the organic solvent, a method in which the polyglycolic acid is subjected to solid phase depolymerization, and so on.

The molecular weight of the polyglycolic acid used in the production of the glycolide can be set as appropriate in accordance with the reaction conditions and so on. The molecular weight of the polyglycolic acid is usually approximately 5,000 to 150,000, preferably 8,000 to 100,000, in terms of the weight average molecular weight. The form of the polyglycolic acid can be made to be any chosen form, for example lumps, pellets, granules or a powder, but it is preferable to make the polyglycolic acid into fine granules by pulverization or the like, since then the surface area is increased and hence the reaction is promoted.

When depolymerizing the polyglycolic acid, a publicly known catalyst may be used if necessary. Examples are tin compounds, antimony compounds, or the like.

The reaction temperature in the case of producing glycolide through solid phase depolymerization of the polyglycolic acid is usually approximately 180 to 280° C., preferably approximately 210 to 250° C. By making the reaction temperature be in such a range, glycolide can be produced with a higher yield, and moreover this is also preferable from the standpoint of operability.

In the case of the method in which some or all of the polyglycolic acid is dissolved in an organic solvent, depolymerization is carried out, and the glycolide produced is distilled off with the organic solvent, as the organic solvent used, it is preferable to use a polar organic solvent, with it being particularly preferable to use a polar organic solvent having a boiling point of approximately 200 to 400° C. Examples of such organic solvents are aromatic dicarboxylic acid diesters, aliphatic dicarboxylic acid diesters, polyalkylene glycol diethers, and so on, with polyalkylene glycol diethers being particularly preferable. Of polyalkylene glycol diethers, polyethylene glycol dialkyl ethers such as triethylene glycol dimethyl ether, triethylene glycol diethyl ether, tetraethylene glycol dimethyl ether and tetraethylene glycol diethyl ether are preferable.

With a conventional method of producing a high-purity glycolic acid ester from a relatively inexpensive starting material, industrial grade glycolic acid is used as the starting material, and hence it has been necessary to pass through a large number of steps such as recrystallization, oligomerization, alcoholysis and distillation. The process of producing a glycolic acid ester in the present invention involves a one-step reaction, and the glycolic acid ester obtained through this process can easily be made into a high-purity glycolic acid ester through simple purification means. By using a glycolic acid ester obtained through the above-mentioned production process and/or glycolic acid obtained via the above-mentioned production process as starting material(s), high-purity polyglycolic acid can thus be produced easily and with excellent economy.

The glycolic acid ester and glycolic acid used in the present invention substantially do not contain impurities that would inhibit obtaining a high molecular weight. As a result, according to the present invention polyglycolic acid of high quality and high molecular weight can easily be obtained. According to the present invention, it is thus possible to produce polyglycolic acid having excellent properties such as gas barrier ability and mechanical strength. Moreover, polyglycolic acid of high quality and high molecular weight can be produced without going via glycolide, and hence the polyglycolic acid can be produced simply and economically.

Conventionally, in the case of producing glycolide through the depolymerization of polyglycolic acid, the reaction bottom has become highly viscous, and hence continuous production has been difficult. According to the present invention, the amount of impurities that cause the reaction bottom to become highly viscous is low, and hence increase in the viscosity of the reaction bottom is suppressed, and thus it becomes possible to produce glycolide continuously.

According to the production method of the present invention, polyglycolic acid substantially not containing formaldehyde and chlorine can be obtained.

According to the method of the present invention, depending on the conditions, polyglycolic acid having an amply high molecular weight can also be obtained. The polyglycolic acid obtained through the method of the present invention is also biodegradable, and hence can be favorably used, for example, as a medical material (suture), a general-purpose synthetic resin substitute (gas barrier film), and so on.

BEST MODE FOR CARRYING OUT THE INVENTION

Examples will now be given to further clarify the characteristic features of the present invention. Note, however, that the scope of the present invention is not limited to the scope of the examples.

In the examples, measurement of properties and so on was carried out using the following methods.

(1) Amount Loaded of Fine Metal Particles

This was measured using X-ray fluorescence analysis.

(2) Average Particle Diameter of Fine Metal Particles

The particle diameter was examined using a transmission electron microscope (TEM) (model 'HF-2000', Hitachi, Ltd., accelerating voltage 200 kV), and compositional analysis of the particles was carried out using an attached X-ray analyzer.

(3) Quantification of Reaction Products

Quantitative analysis of the reaction product components in the reaction liquid was carried out using gas chromatography and/or liquid chromatography.

(4) Conversion, Selectivity, and Yield

The conversion, the selectivity, and the yield were calculated based on the following equations.

$$\text{Conversion (\%)} = (1 - B/A) \times 100$$

$$\text{Selectivity (\%)} = \{C/(A-B)\} \times 100$$

$$\text{Yield (\%)} = (C/A) \times 100$$

(In the three equations above, A represents the number of mols of 1,2-diol supplied, B represents the number of mols of 1,2-diol remaining after the reaction, and C represents the number of mols of 1,2-diol consumed in accordance with the number of mols of α-hydroxycarboxylic acid ester produced.)

(5) Weight-Average Molecular Weight

This was determined through comparison with a standard sample (polymethyl methacrylate) using gel permeation chromatography (column temperature 40° C., hexafluoroisopropanol solvent).

EXAMPLE 1-1

<Au Catalyst Reaction Example, EG+MeOH>

(1) Preparation of Catalyst: Preparation of Au/Al—SiO$_2$ (i) Production of Al—SiO$_2$ Carrier An aqueous solution containing aluminum nitrate was loaded by impregnating into a commercially sold silica carrier (made by Fuji Silysia Chemical Ltd., trade name: Cariact) such that the content would become 10 wt % in terms of Al$_2$O$_3$. After that, the water was distilled off, and calcination was carried out for 4 hours at 600° C. in air, thus obtaining an Al—SiO$_2$ carrier.

(ii) Loading of Gold 0.5 L of a 20 mmol/L tetrachloroauric acid aqueous solution was adjusted to pH7 using a 0.5N sodium hydroxide aqueous solution in a range of 65 to 70° C. 20 g of the above-mentioned Al—SiO$_2$ carrier was put into the aqueous solution with stirring, and then the stirring was continued for 1 hour while maintaining the temperature at 65 to 70° C. After that, the system was left to stand, and the supernatant liquid was removed. 0.5 L of ion exchange water was added to the remaining gold-fixed material and stirring was carried out for 5 minutes at room temperature, and then the supernatant liquid was removed; this washing process was repeated three times. Filtration was then carried out, and the gold-fixed material thus obtained was dried for 10 hours at 100° C., and was then calcined for 3 hours at 400° C. in air, thus obtaining a catalyst in which gold was loaded on an Al—SiO$_2$ carrier (Au/Al—SiO$_2$). The amount loaded of the gold in the gold-fixed carrier was 4.2 wt % relative to the carrier. Moreover, upon examining the particle diameter of the fine gold particles supported on the catalyst, it was found that almost all of the gold was highly dispersed in the form of particles having a particle diameter of not more than 6 nm, a narrow particle diameter distribution having a maximum at around 2 to 3 nm was exhibited, and the average particle diameter was not more than 6 nm.

(2) Oxidative Esterification Reaction (Production of α-hydroxycarboxylic Acid Ester)

Synthesis of an α-hydroxycarboxylic acid ester was carried out using the Au/Al—SiO$_2$ catalyst obtained in (1) above.

3.1 g (50 mmol) of ethylene glycol, 16 g (0.5 mol) of methanol, and 1.5 g of the above-mentioned catalyst were put into a rotating stirring type 100 mL autoclave, and the autoclave was hermetically sealed. 0.2 Mpa of nitrogen and 0.3 Mpa of oxygen were put in in this order, and then the temperature was raised to 90° C. while stirring and reaction was carried out for 4 hours while successively feeding in oxygen such that the pressure remained constant. After that, cooling was carried out, and the autoclave was opened; upon analyzing the contents using gas chromatography, it was found that the conversion of the ethylene glycol starting material was 64.8%, and the selectivities of the products methyl glycolate, 2-hydroxymethyl glycolate, dimethyl oxalate, and other oxalic acid compounds (oxalic acid etc.) were 82.5%, 14.6%, 1.2% and 0.1% respectively. Moreover, the molar production ratios for methyl formate and 2-hydroxyethyl formate relative to methyl glycolate were 0.24 and 0.01 respectively.

EXAMPLE 1-2

<Pd Catalyst Reaction Example, EG+MeOH>

Ion exchange water was added to 20 mL of a tetraamminepalladium hydroxide aqueous solution (20 g/L in terms of Pd metal, made by Tokuriki Honten Co., Ltd., [Pd(NH$_3$)$_4$](OH)$_2$) to make the total amount 400 mL, and the system was heated to 70° C. 10 g of the Al—SiO$_2$ carrier prepared in Example 1-1 was added to the solution with stirring, and then the stirring was continued for 1 hour while maintaining the temperature at 70° C. After that, washing with water was carried out three times as in Example 1-1. Filtration was then carried out, and the palladium-fixed material thus obtained was dried for 10 hours at 100° C., and was then calcined for 3 hours at 400° C. in air. After the calcination, 2 g of the palladium-fixed material was filled into a glass tube, and with the temperature maintained at 350° C., a mixed gas of hydrogen and nitrogen (hydrogen to nitrogen volume ratio=1:9) was passed through the tube for 2 hours at a flow rate of 80 mL/min. A catalyst in which metallic palladium was loaded on an Al—SiO$_2$ carrier (Pd/Al—SiO$_2$) was thus obtained. The amount loaded of the palladium in the fixed material was 2.8 wt % relative to the carrier. Moreover, upon examining the particle diameter of the palladium particles loaded on the catalyst, it was found that almost all of the palladium was highly dispersed in the form of particles having a particle diameter of not more than 6 nm, a narrow particle diameter distribution having a maximum at around 2 to 4 nm was exhibited, and the average particle diameter was not more than 6 nm.

(2) Oxidative Esterification Reaction (Production of α-hydroxycarboxylic Acid Ester)

An α-hydroxycarboxylic acid ester was synthesized as in Example 1-1, except that the Pd/Al—SiO$_2$ catalyst obtained in (1) above was used.

Upon analyzing the products after the reaction using gas chromatography, it was found that the conversion of the ethylene glycol starting material was 50.4%, and the selectivity of the product methyl glycolate was 53.5%. Moreover, the molar production ratio for methyl formate relative to methyl glycolate was 1.63.

EXAMPLE 1-3

<Ru Catalyst Reaction Example, EG+MeOH>

Ion exchange water was added to 34.6 g of a tetraammineruthenium hydroxide aqueous solution (0.72 wt % in terms of Ru metal, made by Tanaka Kikinzoku K.K., [Ru(NH$_3$)$_4$](OH)$_2$) to make the total amount 400 mL, and the system was heated to 70° C. 10 g of the Al—SiO$_2$ carrier prepared in Example 1-1 was added to the solution with stirring, and then the stirring was continued for 1 hour while maintaining the temperature at 70° C. After that, washing with water was carried out three times as in Example 1-1. Filtration was then carried out, and the ruthenium-fixed material thus obtained was dried for 10 hours at 100° C., and was then calcined for 3 hours at 400° C. in air. After the calcination, 2 g of the ruthenium-fixed material was filled into a glass tube, and with the temperature maintained at 350° C., a mixed gas of hydrogen and nitrogen (hydrogen to nitrogen volume ratio=1:9) was passed through the tube for 2 hours at a flow rate of 80 mL/min. A catalyst in which metallic ruthenium was loaded on an Al—SiO$_2$ carrier (Ru/Al—SiO$_2$) was thus obtained. The amount loaded of the ruthenium in the fixed material was 2.4 wt % relative to the carrier. Moreover, upon examining the particle diameter of the ruthenium particles loaded on the catalyst, it was found that almost all of the ruthenium was highly dispersed in the form of particles having a particle diameter of not more than 6 nm, a narrow particle diameter distribution having a maximum at around 2 to 4 nm was exhibited, and the average particle diameter was not more than 6 nm.

(2) Oxidative Esterification Reaction (Production of α-hydroxycarboxylic Acid Ester)

An α-hydroxycarboxylic acid ester was synthesized as in Example 1-1, except that the Ru/Al—$SiO_2$ catalyst obtained in (1) above was used, and the reaction temperature was made to be 100° C.

Upon analyzing the products after the reaction using gas chromatography, it was found that the conversion of the ethylene glycol starting material was 6.4%, and the selectivity of the product methyl glycolate was 76.2%. Moreover, the molar production ratio for methyl formate relative to methyl glycolate was 1.26.

EXAMPLE 1-4

<Pb—Au Alloy Catalyst Reaction Example, EG+MeOH>

(1) Preparation of Catalyst

Using a $TiO_2$—$SiO_2$ carrier prepared using a coprecipitation method (Ti/Si molar ratio=8:2, calcination temperature 600° C., 50 to 250 mesh), Au was loaded as in Example 1-1, thus obtaining Au/$TiO_2$—$SiO_2$.

Next, 20 g of the Au/$TiO_2$—$SiO_2$ gold-fixed material was added to 50 mL of a methanol solution containing 1.835 g of lead acetate trihydrate, and using an evaporator, the methanol was removed at 80° C. and normal pressure, thus impregnating and supporting the lead acetate. After that, 20 g of the gold-fixed material having lead loaded thereon was filled into a glass tube, and heating was carried out for 3 hours at 400° C. while passing through a mixed gas of hydrogen and nitrogen (volume ratio 10/90). A gold alloy-fixed material in which metal particles containing gold and lead were loaded on a $TiO_2$—$SiO_2$ carrier was thus obtained. The amounts loaded of the gold and the lead in the fixed material were 5.4 wt % and 4.9 wt % respectively relative to the carrier. Moreover, upon examining the particle diameter of the metal particles, it was found that almost all of the metal was highly dispersed in the form of particles having a particle diameter of not more than 6 nm, a narrow particle diameter distribution having a maximum at around 2 to 3 nm was exhibited, and the average particle diameter was not more than 6 nm.

(2) Oxidative Esterification Reaction (Production of α-hydroxycarboxylic Acid Ester)

Synthesis of an α-hydroxycarboxylic acid ester was carried out using the Pb—Au alloy/$TiO_2$—$SiO_2$ catalyst obtained in (1) above.

62 g (1.0 mol) of ethylene glycol, 320 g (10 mol) of methanol, and 20 g of the above-mentioned catalyst were put into a rotating stirring type 1 L autoclave having a condenser tube, and the autoclave was hermetically sealed. Next, a mixed gas of oxygen and nitrogen (volume ratio 10/90) was blown into the liquid at a flow rate of 1 L/min while adjusting using a back pressure valve such that the pressure inside the system was maintained at 0.5 Mpa, and reaction was carried out for 5 hours at 90° C. while carrying out this bubbling.

After that, cooling was carried out, and the autoclave was opened; upon analyzing the contents using gas chromatography, it was found that 0.180 mol of the ethylene glycol starting material was contained, and the contents of the products methyl glycolate, 2-hydroxyethyl glycolate, glycolide, dimethyl oxalate, and other oxalic acid compounds (oxalic acid etc.) were 0.656 mol, 0.068 mol, 0.012 mol, 0.008 mol and 0.001 mol respectively. Moreover, the molar production ratios for methyl formate and 2-hydroxyethyl formate relative to methyl glycolate were 0.12 and 0.03 respectively.

EXAMPLE 1-5

<Au/Ti—$SiO_2$ Catalyst Reaction Example, EG+MeOH>

(1) Preparation of Catalyst: Preparation of Au/Ti—$SiO_2$ (i) Production of Ti—$SiO_2$ Carrier A 2-propanol solution containing titanium tetra-n-butoxide was loaded by impregnating into a commercially sold silica carrier (made by Fuji Silysia Chemical Ltd., trade name: Cariact) such that the content would become 15 wt % in terms of $TiO_2$. After that, the 2-propanol was distilled off, and calcination was carried out for 4 hours at 600° C. in air, thus obtaining a Ti—$SiO_2$ carrier.

(ii) Supporting of Gold

An Au/Ti—$SiO_2$ catalyst in which gold was loaded on a Ti—$SiO_2$ carrier was obtained using the same procedure as in Example 1-1, except that 1.5 L of a 14 mmol/L tetrachloroauric acid aqueous solution was used, and moreover 50 g of the above-mentioned Ti—$SiO_2$ was used as the carrier. The amount loaded of the gold in the gold-fixed material was 5.8 wt % relative to the carrier. Moreover, upon examining the particle diameter of the fine gold particles loaded on the catalyst, it was found that almost all of the gold was highly dispersed in the form of particles having a particle diameter of not more than 6 nm, a narrow particle diameter distribution having a maximum at around 2 to 3 nm was exhibited, and the average particle diameter was not more than 6 nm.

(2) Oxidative Esterification Reaction (Production of α-hydroxycarboxylic Acid Ester)

Synthesis of an α-hydroxycarboxylic acid ester was carried out using the Au/Al—$SiO_2$ catalyst obtained in (1) above.

165 g (2.66 mol) of ethylene glycol, 426 g (13.3 mol) of methanol, and 20 g of the above-mentioned catalyst were put into a rotating stirring type 1 L autoclave having a condenser tube, and the autoclave was hermetically sealed. Next, a mixed gas of oxygen and nitrogen (volume ratio 8/92) was blown into the liquid at a flow rate of 0.8 L/min while adjusting using a back pressure valve such that the pressure inside the system was maintained at 1 Mpa, and reaction was carried out for 6 hours at a reaction temperature of 110° C. while carrying out the gas bubbling. After that, cooling was carried out, and the autoclave was opened; upon analyzing the contents using gas chromatography, it was found that the conversion of the ethylene glycol starting material was 62%, and the selectivities of the products methyl glycolate, 2-hydroxyethyl glycolate, and glycolic acid were 69 mol %, 20 mol % and 4 mol % respectively.

EXAMPLE 1-6

<Au/Ti—$SiO_2$ Catalyst Reaction Example, EG Alone>

533 g (8.58 mol) of ethylene glycol, and 17 g of the catalyst obtained in Example 1-5 were put into a rotating stirring type autoclave (1 L) having a condenser tube, and the autoclave was hermetically sealed. Next, a mixed gas of oxygen and nitrogen (volume ratio 10:90) was blown into the liquid at a flow rate of 0.8 L/min while adjusting using a back pressure valve such that the pressure inside the system was maintained at 2 Mpa, and reaction was carried out for 9 hours at a reaction temperature of 110° C. while carrying out the gas bubbling. After that, cooling was carried out, and the autoclave was opened; upon analyzing the contents using gas chromatography, it was found that the conversion of the ethylene glycol starting material was 52%, and the selectivities of the products 2-hydroxyethyl glycolate and glycolic acid were 72 mol % and 5 mol % respectively.

EXAMPLE 1-7

<Removal of Oxalic Acid Esters from the Reaction Liquid of Example 1-4, Followed by Purification of Glycolic Acid Ester>

The reaction liquid (404.9 g) obtained by separating away the catalyst after the oxidative esterification reaction in Example 1-4 contained ethylene glycol and methanol as residual starting materials, the reaction products, and water produced in the reaction. Out of the contents there was a total of 0.011 mol of oxalic acid esters, that is 0.008 mol (0.92 g) of dimethyl oxalate and 0.001 mol of other oxalic acid compounds (oxalic acid etc.).

3 mL of a methanol solution containing 0.013 mol (1.44 equivalents) of the magnesium salt of glycolic acid was added to the reaction solution, and then all of the solution was put into a 1 L autoclave, and after purging with nitrogen, the temperature was raised to 80° C. and stirring was carried out for 2 hours. After that, cooling was carried out, and the autoclave was opened, whereupon it was found that a white precipitate of magnesium oxalate had been produced. Then, after filtering, the reaction liquid was analyzed using gas and liquid chromatography, whereupon it was found that the signals corresponding to dimethyl oxalate and other oxalic acid compounds had virtually disappeared.

Next, after filtering off the magnesium oxalate, methanol and water were distilled off from the obtained solution under reduced pressure using a thin-layer distillation apparatus. After that, the methyl glycolate was distilled off using a 3-stage glass distillation column with a bottom temperature of 70 to 80° C. at a pressure of 5 to 10 torr. The purity of the methyl glycolate in the distillate was greater than 98 wt %; a total of approximately 1.5 wt % of methanol and water was contained, but the content of other impurities was less than 0.1 wt %. The total content of dimethyl oxalate and other oxalic acid compounds was not more than 100 ppm by weight.

EXAMPLE 2-1

<Pb—Au Alloy Catalyst Reaction Example, EG+MeOH>

(1) Preparation of Catalyst $TiO_2$—$SiO_2$ prepared using a coprecipitation method (Ti/Si molar ratio=8:2, calcination temperature 600° C., 50 to 250 mesh) was used as a carrier.

0.5 L of a 20 mmol/L tetrachloroauric acid aqueous solution was adjusted to pH7 using a 0.5N sodium hydroxide aqueous solution in a range of 65 to 70° C. 20 g of the above-mentioned $TiO_2$—$SiO_2$ carrier was put into the aqueous solution with stirring, and then the stirring was continued for 1 hour while maintaining the temperature at 65 to 70° C. After that, the system was left to stand, and the supernatant liquid was removed. 0.5 L of ion exchange water was added to the remaining gold-fixed material and stirring was carried out for 5 minutes at room temperature, and then the supernatant liquid was removed; this washing process was repeated three times. Filtration was then carried out, and the gold-fixed material thus obtained was dried for 10 hours at 100° C., and was then calcined for 3 hours at 400° C. in air, thus obtaining a catalyst in which gold was supported on a $TiO_2$—$SiO_2$ carrier (Au/$TiO_2$—$SiO_2$).

Next, 20 g of the above-mentioned Au/$TiO_2$—$SiO_2$ gold-fixed material was added to 50 mL of a methanol solution containing 1.835 g of lead acetate trihydrate, and using an evaporator, the methanol was removed at 80° C. and normal pressure, thus impregnating and supporting the lead acetate. After that, 20 g of the gold-fixed material having lead loaded thereon was filled into a glass tube, and heating was carried out for 3 hours at 400° C. while passing through a mixed gas of hydrogen and nitrogen (volume ratio 10/90). A gold alloy-fixed material in which metal particles containing gold and lead were loaded on a $TiO_2$—$SiO_2$ carrier was thus obtained. The amounts loaded of the gold and the lead in the loaded material were 5.4 wt % and 4.9 wt % respectively relative to the carrier. Moreover, upon examining the particle diameter of the metal particles, it was found that almost all of the metal was highly dispersed in the form of particles having a particle diameter of not more than 6 nm, a narrow particle diameter distribution having a maximum at around 2 to 3 nm was exhibited, and the average particle diameter was not more than 6 nm.

(2) Oxidative Esterification Reaction (Production of α-hydroxycarboxylic Acid Ester)

Synthesis of an α-hydroxycarboxylic acid ester was carried out using the Pb—Au alloy/$TiO_2$—$SiO_2$ catalyst obtained in (1) above.

62 g (1.0 mol) of ethylene glycol, 320 g (10 mol) of methanol, and 20 g of the above-mentioned catalyst were put into a rotating stirring type 1 L autoclave having a condenser tube, and the autoclave was hermetically sealed. Next, a mixed gas of oxygen and nitrogen (volume ratio 10/90) was blown into the liquid at a flow rate of 1 L/min while adjusting using a back pressure valve such that the pressure inside the system was maintained at 0.5 Mpa, and reaction was carried out for 5 hours at 90° C. while carrying out this bubbling.

After that, cooling was carried out, and the autoclave was opened; upon analyzing the contents using gas chromatography, it was found that 0.180 mol of the ethylene glycol starting material was contained, and the contents of the products methyl glycolate, 2-hydroxyethyl glycolate, glycolide, dimethyl oxalate, and other oxalic acid compounds were 0.656 mol, 0.068 mol, 0.012 mol, 0.008 mol and 0.001 mol respectively. Moreover, the molar production ratios for methyl formate and 2-hydroxyethyl formate relative to methyl glycolate were 0.12 and 0.03 respectively.

(3) Removal of Oxalic Acid Esters, Followed by Purification of Glycolic Acid Ester The reaction filtrate (404.9 g) obtained by separating away the catalyst from the reaction liquid obtained through the oxidative esterification reaction of (2) above contained ethylene glycol and methanol as residual starting materials, the reaction products, and water produced in the reaction. Out of the contents there was a total of 0.011 mol of oxalic acid esters, that is 0.008 mol (0.92 g) of dimethyl oxalate and 0.001 mol of other oxalic acid compounds (oxalic acid etc.).

3 mL of a methanol solution containing 0.013 mol of the magnesium salt of glycolic acid was added to the reaction solution, and then all of the solution was put into a 1 L autoclave, and after purging with nitrogen, the temperature was raised to 80° C. and stirring was carried out for 2 hours. After that, cooling was carried out, and the autoclave was opened, whereupon it was found that a white precipitate of magnesium oxalate had been produced. Then, after filtering, the reaction liquid was analyzed using gas chromatography, whereupon it was found that the signals corresponding to dimethyl oxalate and other oxalic acid compounds had virtually disappeared.

After filtering off the magnesium oxalate, methanol and water were distilled off from the obtained filtrate under reduced pressure using a thin-layer distillation apparatus. After that, the methyl glycolate was distilled off using a 3-stage glass distillation column with a bottom temperature of 70 to 80° C. at a pressure of 5 to 10 torr. The purity of the methyl glycolate in the distillate was greater than 98 wt %; a total of approximately 1.5 wt % of methanol and water was contained, but the content of other impurities was less than 0.1 wt %. The total content of dimethyl oxalate and other oxalic acid compounds (oxalic acid etc.) was less than 100 ppm by weight.

(4) Hydrolysis Reaction (Hydrolysis by Reactive Distillation)

As a reactive distillation apparatus, an apparatus obtained by connecting a 3-stage packed column to a flask and further providing a refluxing device at the top of the packed column was used. A mixed liquid obtained by mixing 150 g of water with 50 g of the distillate containing more than 98 wt % of methyl glycolate obtained in (3) above was put into the flask. Next, reactive distillation was carried out for 2 hours at normal pressure, maintaining the temperature at the base of the column of the reactive distillation apparatus (i.e. the liquid temperature) at 95 to 97° C. At this time, distillate containing methanol was distilled off. The temperature at the top of the column was 65° C. at the start of the reactive distillation, but had reached 100° C. by the end.

After the reactive distillation had been completed, 114 g of an aqueous solution containing 36.1 wt % of glycolic acid was recovered from the flask. The yield of glycolic acid relative to the methyl glycolate was 100%. Regarding impurities, formaldehyde and chlorine compounds were not detected, and 20 ppm of oxalic acid and 76 ppm of ethylene glycol were detected.

EXAMPLE 3-1

<Production of Polyglycolic Acid Through Polycondensation of Methyl Glycolate>

100 mg of the methyl glycolate obtained in Examples 1-4 and 1-7 and 0.1 g of stannic chloride were put into a stainless steel stirring type autoclave (200 mL), and after purging with nitrogen, the internal pressure was made to be a gauge pressure of 0.2 Mpa using nitrogen, and then reaction was carried out for 10 hours at 150° C. while stirring. After that, the polycondensation was carried out for a further 3 hours while flushing produced methanol out of the system by passing dry nitrogen through the reaction liquid at 500 mL/min. Cooling was then carried out to room temperature, and a white solid was recovered.

The polyglycolic acid obtained had a melting point of 202° C., and a weight average molecular weight of 60,000.

EXAMPLE 3-2

<Production of Polyglycolic Acid by Polycondensation of Glycolic Acid Ester>

50 g of the methyl glycolate obtained in Examples 1-4 and 1-7, 200 g of tetraethylene glycol dimethyl ether, and 0.5 g of titanium tetrabutoxide were put into a reactor equipped with a Dean-Stark trap, and a condensation polymerization reaction was carried out for 10 hours at 150° C. while stirring. At this time, the polycondensation reaction was carried out while passing dry nitrogen through the reaction liquid at 500 mL/min, thus distilling produced methanol out of the system.

After that, the Dean-Stark trap was taken off, and a tube filled with 10 g of molecular sieve 4A was attached. Reaction was carried out for a further 24 hours at 160° C. under reduced pressure (3 kPa) without passing through nitrogen such that the outflowing solvent passed through the molecular sieve and then returned into the system. The weight average molecular weight of the polyglycolic acid obtained was 100,000.

EXAMPLE 3-3

<Production of Polyglycolic Acid Having Yet Higher Molecular Weight by Polycondensation of Polyglycolic Acid>

The polyglycolic acid obtained in Example 3-1 was pulverized in a mortar. 50 g of the powder obtained was put into a 200 mL flask. Solid phase polymerization was carried out for 3 hours at 200° C. while passing through dry nitrogen at a flow rate of 500 mL/min and maintaining the internal pressure at 0.1 kPa, and then solid phase polymerization was further carried out for 24 hours at 220° C. The melting point of the polyglycolic acid obtained was 226° C., and the weight average molecular weight was 250,000. Formaldehyde and chlorine were not detected in the polyglycolic acid obtained.

EXAMPLE 3-4

<Production of Glycolide by Depolymerization of Polyglycolic Acid>

50 g of the polyglycolic acid obtained in Example 3-1 and 300 g of triethylene glycol dimethyl ether were put into a 500 mL flask. Heating was carried out to 250° C. while stirring, and then the internal pressure was set to 2 kPa and the solvent and glycolide were distilled off together. This state was maintained for 5 hours, whereby 260 g of distillate containing 32 g of glycolide was obtained. Double the volume of cyclohexane was added to the distillate obtained, thus precipitating out the glycolide from the triethylene glycol dimethyl ether, and then the glycolide was recovered by filtration. The glycolide obtained was recrystallized using ethyl acetate, and drying was carried out under reduced pressure. The yield was 61%.

EXAMPLE 3-5

<Production of Glycolide by Depolymerization of Polyglycolic Acid>

Using the polyglycolic acid containing tetraethylene glycol dimethyl ether obtained in Example 3-2 as a starting material, depolymerization into glycolide was carried out. Specifically, additional tetraethylene glycol dimethyl ether was added to the tetraethylene glycol dimethyl ether solution containing polyglycolic acid obtained in Example 3-2 in a 500 mL flask, thus making the total amount 200 g. The solution was then maintained at 260° C. while stirring, and the internal pressure was set to 2 kPa and the solvent and glycolide were distilled off together. The temperature was maintained at 260° C. for 5 hours, whereby 190 g of distillate containing 20 g of glycolide was obtained.

What is claimed is:

1. A method of producing a diol derivative, comprising a step of obtaining an α-hydroxycarboxylic acid ester by reacting (i) one or more 1,2-diols or (ii) a 1,2-diol and a primary alcohol as starting material(s) with oxygen in the presence of a catalyst comprising metal loaded on a carrier.

2. The method according to claim 1, wherein the metal loaded on the carrier is a metal other than gold.

3. The method according to claim 1, wherein ethylene glycol and a primary alcohol are used as the starting materials.

4. The method of producing a diol derivative according to claim 1, further comprising a step of hydrolyzing the obtained α-hydroxycarboxylic acid ester to obtain an α-hydroxycarboxylic acid.

5. The method according to claim 4, wherein the metal loaded on the carrier comprises gold and at least one metal other than gold.

6. The method of producing a diol derivative according to claim 4, further comprising a step of subjecting the obtained α-hydroxycarboxylic acid to polycondensation to obtain polyglycolic acid.

7. The method according to claim 6, further comprising a step of subjecting the obtained polyglycolic acid to further polycondensation to produce polyglycolic acid having a higher molecular weight.

8. The method according to claim 6, further comprising a step of subjecting the obtained polyglycolic acid to depolymerization to obtain glycolide.

9. The method of producing a diol derivative according to claim 1, further comprising a step of subjecting the obtained α-hydroxycarboxylic acid ester to polycondensation to obtain polyglycolic acid.

10. The method according to claim 9, further comprising a step of subjecting the obtained polyglycolic acid to further polycondensation to produce polyglycolic acid having a higher molecular weight.

11. The method according to claim 9, further comprising a step of subjecting the obtained polyglycolic acid to depolymerization to obtain glycolide.

12. The method according to claim 9, wherein the metal loaded on the carrier comprises gold and at least one metal other than gold.

* * * * *